(12) United States Patent
Dardick et al.

(10) Patent No.: US 9,371,536 B2
(45) Date of Patent: Jun. 21, 2016

(54) PPETAC1 GENE AND METHOD TO MANIPULATE TREE ARCHITECTURE

(71) Applicant: The United States of America, as represented by the Secretary of Agriculture, Washington, DC (US)

(72) Inventors: Christopher D. Dardick, Shenandoah Junction, WV (US); Ann M. Callahan, Shepherdstown, WV (US); Ralph Scorza, Shepherdstown, WV (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/243,118

(22) Filed: Apr. 2, 2014

(65) Prior Publication Data

US 2014/0304852 A1  Oct. 9, 2014

Related U.S. Application Data

(60) Provisional application No. 61/808,269, filed on Apr. 4, 2013.

(51) Int. Cl.
*C12N 15/82* (2006.01)
*A01H 5/08* (2006.01)
*A01H 1/04* (2006.01)
*C07K 14/415* (2006.01)
*C12Q 1/68* (2006.01)

(52) U.S. Cl.
CPC .............. *C12N 15/8261* (2013.01); *A01H 1/04* (2013.01); *C07K 14/415* (2013.01); *C12N 15/8218* (2013.01); *C12Q 1/6895* (2013.01); *C12Q 2600/13* (2013.01)

(58) Field of Classification Search
None
See application file for complete search history.

(56) References Cited

PUBLICATIONS de Muro (Medical Biomethods Handbook, Humana Press, 2005 p. 13-23).*
Wang (Genbank Accession JP706780, Nov. 21, 2011).*

* cited by examiner

*Primary Examiner* — Anne Kubelik
*Assistant Examiner* — Charles Logsdon
(74) *Attorney, Agent, or Firm* — John D. Fado; Evelyn M. Rabin

(57) ABSTRACT

Disclosed is a novel gene that controls the branching angle of a tree wherein either silencing or overexpressing PpeTAC1 controls the architecture of transformed to the tree.

16 Claims, 14 Drawing Sheets

Standard (*BrBr*)

Upright (*Brbr*)

**Vertical branching (*brbr*)**

SEQUENCE LISTING

<160> NUMBER OF SEQ ID NOS: 27

<210> SEQ ID NO 1
<211> LENGTH: 909
<212> TYPE: DNA
<213> ORGANISM: Prunus persica

<400> SEQUENCE: 1

```
atgaagatct tcaactgggt tcataagagg cttcatcaaa gggtcgtcaa ggatgggttt      60
gctgggaatg tgaaaaagag tgaactggaa accaatgaca aggacacaca agcatttctc     120
aaacaagttg gccttgttaa tgtggatggg cttgatggtt ggagggatgg cattttaact     180
```

```
ataggcacct ttggtttcga cccctaaaa ccctctaccc accaaaacga atatttcgtt    240
ctggagagcg aagaagacga tcaggaaagc catggatttt cacacagtgg taatgatgat    300
gatgatgatg atgatgaaca ttatgatcat agtgttgaag atgaagaact gaacccttta    360
atgtttacaa catttgaaca cagctttgag gatattgggt caaattttga tgccattgtt    420
cagaaaccag ctgatgtgat cctgaccgtt gatggtgtcc ctcttactcc atttgagggg    480
tccagtgaaa tcagtactaa acctgatcag agtgctaatg atcagagcaa gaataagaaa    540
ggtcagagaa ttacactggc tgacttgttc caggctgatg ttcctgatgt tggtcaactg    600
aagcttgact ctggcaaggt ccagccagaa atggagaaaa aaatgaatgc cagaacaagg    660
agtggcctag catttgccaa gaaactcatc cctcgcgtca agatgattc aagtccaatc     720 aaaaatatgc aacgactgat gaggaggatg ttgaagagga agatccatcc agctgagctt    780
gaagtcaaga ttcacaaatc agatggccag aagcagccca gtgcggtaga gctcatctcc    840
aatgtcgaaa atgatgctta tgaatcggtt tctttgcttc caattcaagg tgccccttgt    900
gtgcactga                                                             909

<210> SEQ ID NO 2
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 2
tgaaccactt gtgcttctgc ga                                              22

<210> SEQ ID NO 3
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 3
attcaaacag cagccacaac gg                                              22

<210> SEQ ID NO 4
<211> LENGTH: 21
<212> TYPE: DNA
<213> ORGANISM: Artificial Sequence
<220> FEATURE:
<223> OTHER INFORMATION: Primer used in expression analysis of PpeTAC1

<400> SEQUENCE: 4
ggaaatgcaa ataggaattg g                                               21

<210> SEQ ID NO 5
<211> LENGTH: 20
<212> TYPE: DNA
<213> ORGANISM: Artificial Sequence
<220> FEATURE:
<223> OTHER INFORMATION: Primer used in expression analysis of PpeTAC1

<400> SEQUENCE: 5
ctctctctct gtggattaaa                                                 20

<210> SEQ ID NO 6
<211> LENGTH: 22
<212> TYPE: DNA
```

```
<213> ORGANISM: Artificial Sequence
<220> FEATURE:
<223> OTHER INFORMATION: Primer used in expression analysis of PpeTAC1

<400> SEQUENCE: 6
ctcacatggc catagggata gt                                              22

<210> SEQ ID NO 7
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 7
tgaaagacgt acgccaagcc aa                                              22

<210> SEQ ID NO 8
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 8
agagcgaaga agacgatcag ga                                              22

<210> SEQ ID NO 9
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 9
cagctggttt ctgaacaatg gc                                              22

<210> SEQ ID NO 10
<211> LENGTH: 20
<212> TYPE: DNA
<213> ORGANISM: Artificial Sequence
<220> FEATURE:
<223> OTHER INFORMATION: Primer used in expression analysis of PpeTAC1

<400> SEQUENCE: 10
aagcacacgt tccactctgt                                                 20

<210> SEQ ID NO 11
<211> LENGTH: 24
<212> TYPE: DNA
<213> ORGANISM: Artificial Sequence
<220> FEATURE:
<223> OTHER INFORMATION: Primer used in expression analysis of PpeTAC1

<400> SEQUENCE: 11
ggcaatagtt gtgtgaggtg aggt                                            24

<210> SEQ ID NO 12
<211> LENGTH: 24
<212> TYPE: DNA
<213> ORGANISM: Artificial Sequence
<220> FEATURE:
<223> OTHER INFORMATION: Primer used in expression analysis of PpeTAC1

<400> SEQUENCE: 12
acagctaagc tcctacttca accc                                            24
```

<210> SEQ ID NO 13
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 13
agagagtggc tttgcttggt ct                                              22

<210> SEQ ID NO 14
<211> LENGTH: 22
<212> TYPE: DNA
<213> ORGANISM: Artificial Sequence
<220> FEATURE:
<223> OTHER INFORMATION: Primer used in expression analysis of PpeTAC1

<400> SEQUENCE: 14
tcttccatct aagctgccac at                                              22

<210> SEQ ID NO 15
<211> LENGTH: 26
<212> TYPE: DNA
<213> ORGANISM: Artificial Sequence
<220> FEATURE:
<223> OTHER INFORMATION: Primer used in expression analysis of PpeTAC1

<400> SEQUENCE: 15
gcagtgaatt gaagaaataa tcgtcg                                          26

<210> SEQ ID NO 16
<211> LENGTH: 27
<212> TYPE: DNA
<213> ORGANISM: Artificial Sequence
<220> FEATURE:
<223> OTHER INFORMATION: Primer used in expression analysis of full
      length PpeTAC1

<400> SEQUENCE: 16
gaattcaatt gctcacaaaa tatgaag                                         27

<210> SEQ ID NO 17
<211> LENGTH: 24
<212> TYPE: DNA
<213> ORGANISM: Artificial Sequence
<220> FEATURE:
<223> OTHER INFORMATION: Primer used in expression analysis of PpeTAC1

<400> SEQUENCE: 17
ggatccttaa ttcagtgcac acaa                                            24

<210> SEQ ID NO 18
<211> LENGTH: 24
<212> TYPE: DNA
<213> ORGANISM: Artificial Sequence
<220> FEATURE:
<223> OTHER INFORMATION: Primer used in expression analysis of PpeTAC1

<400> SEQUENCE: 18
tttgccaaga aactcatccc tcgc                                            24

<210> SEQ ID NO 19
<211> LENGTH: 24
<212> TYPE: DNA
<213> ORGANISM: Artificial Sequence

```
<220> FEATURE:
<223> OTHER INFORMATION: Primer used in expression analysis of PpeTAC1

<400> SEQUENCE: 19
gctgcttctg gccatctgat ttgt                                            24

<210> SEQ ID NO 20
<211> LENGTH: 21
<212> TYPE: DNA
<213> ORGANISM: Artificial Sequence
<220> FEATURE:
<223> OTHER INFORMATION: Forward primer used to detect SEQ. ID. NO. 1

<400> SEQUENCE: 20
aattgctcac aaaatatgaa g                                               21

<210> SEQ ID NO 21
<211> LENGTH: 18
<212> TYPE: DNA
<213> ORGANISM: Artificial Sequence
<220> FEATURE:
<223> OTHER INFORMATION: Reverse primer used to detect SEQ. ID. NO. 1

<400> SEQUENCE: 21
ttaattcagt gcacacaa                                                   18

<210> SEQ ID NO 22
<211> LENGTH: 20
<212> TYPE: DNA
<213> ORGANISM: Artificial Sequence
<220> FEATURE:
<223> OTHER INFORMATION: Forward primer used to assemble a PpeTAC1
      silencing construct in a plum species

<400> SEQUENCE: 22
tgggtttgct gggaatgtga                                                 20

<210> SEQ ID NO 23
<211> LENGTH: 22
<212> TYPE: DNA
<213> ORGANISM: Artificial Sequence
<220> FEATURE:
<223> OTHER INFORMATION: Reverse primer used to assemble a PpeTAC1
      silencing construct in a plum species

<400> SEQUENCE: 23
cagctggttt ctgaacaatg gc                                              22

<210> SEQ ID NO 24
<211> LENGTH: 380
<212> TYPE: DNA
<213> ORGANISM: Prunus persica

<400> SEQUENCE: 24
tgggtttgct gggaatgtga aaagagtga actggaaacc aatgacaagg acacacaagc      60
atttctcaaa caagttggcc ttgttaatgt ggatgggctt gatggttgga gggatggcat    120
tttaactata ggcacctttg gtttcgaccc cctaaaaccc tctacccacc aaaacgaata    180
tttcgttctg gagagcgaag aagacgatca ggaaagccat ggattttcac acagtggtaa    240
tgatgatgat gatgatgatg atgaacatta tgatcatagt gttgaagatg aagaactgaa    300 cccttttaatg tttacaacat ttgaacacag ctttgaggat attgggtcaa attttgatgc    360
cattgttcag aaaccagctg                                                380
```

<210> SEQ ID NO 25
<211> LENGTH: 28
<212> TYPE: DNA
<213> ORGANISM: Artificial Sequence
<220> FEATURE:
<223> OTHER INFORMATION: Primer used to amplify full length PpeTAC1

<400> SEQUENCE: 25
gaattcaatt cgctcacaaa atatgaag                                    28

<210> SEQ ID NO 26
<211> LENGTH: 26
<212> TYPE: DNA
<213> ORGANISM: Artificial Sequence
<220> FEATURE:
<223> OTHER INFORMATION: Reverse used to amplify full length PpeTAC1

<400> SEQUENCE: 26
ccttgtgtgc actgaattaa ggatcc                                      26

<210> SEQ ID NO 27
<211> LENGTH: 302
<212> TYPE: PRT
<213> ORGANISM: Prunus persica

<400> SEQUENCE: 27

Met Lys Ile Phe Asn Trp Val His Lys Arg Leu His Gln Arg Val Val
1               5                   10                  15

Lys Asp Gly Phe Ala Gly Asn Val Lys Lys Ser Glu Leu Glu Thr Asn
            20                  25                  30

Asp Lys Asp Thr Gln Ala Phe Leu Lys Gln Val Gly Leu Val Asn Val
        35                  40                  45

Asp Gly Leu Asp Gly Trp Arg Asp Gly Ile Leu Thr Ile Gly Thr Phe
    50                  55                  60

Gly Phe Asp Pro Leu Lys Pro Ser Thr His Gln Asn Glu Tyr Phe Val
65                  70                  75                  80

Leu Glu Ser Glu Glu Asp Asp Gln Glu Ser His Gly Phe Ser His Ser
                85                  90                  95

Gly Asn Asp Asp Asp Asp Asp Glu His Tyr Asp His Ser Val
            100                 105                 110

Glu Asp Glu Glu Leu Asn Pro Leu Met Phe Thr Thr Phe Glu His Ser
        115                 120                 125

Phe Glu Asp Ile Gly Ser Asn Phe Asp Ala Ile Val Gln Lys Pro Ala
    130                 135                 140

Asp Val Ile Leu Thr Val Asp Gly Val Pro Leu Thr Pro Phe Glu Gly
145                 150                 155                 160

Ser Ser Glu Ile Ser Thr Lys Pro Asp Gln Ser Ala Asn Asp Gln Ser
                165                 170                 175

Lys Asn Lys Lys Gly Gln Arg Ile Thr Leu Ala Asp Leu Phe Gln Ala
            180                 185                 190

Asp Val Pro Asp Val Gly Gln Leu Lys Leu Asp Ser Gly Lys Val Gln
        195                 200                 205

Pro Glu Met Glu Lys Lys Met Asn Ala Arg Thr Arg Ser Gly Leu Ala
    210                 215                 220

Phe Ala Lys Lys Leu Ile Pro Arg Val Lys Asp Ser Ser Pro Ile
225                 230                 235                 240

Lys Asn Met Gln Arg Leu Met Arg Arg Met Leu Lys Arg Lys Ile His
                245                 250                 255

-continued

```
Pro Ala Glu Leu Glu Val Lys Ile His Lys Ser Asp Gly Gln Lys Gln
            260                 265                 270

Pro Ser Ala Val Glu Leu Ile Ser Asn Val Glu Asn Asp Ala Tyr Glu
        275                 280                 285

Ser Val Ser Leu Leu Pro Ile Gln Gly Ala Pro Cys Val His
    290                 295                 300
```

PPETAC1 GENE AND METHOD TO MANIPULATE TREE ARCHITECTURE

CROSS-REFERENCE TO RELATED APPLICATION

This present application claims priority under 35 U.S.C. §119(e) to U.S. Provisional Ser. No. 61/808,269, which was filed on Apr. 4, 2013, and is hereby incorporated by reference.

FIELD OF THE INVENTION

This invention relates to a novel gene that controls the branching angle of a tree. Disclosed is the gene, PpeTAC1, and a method to control tree architecture via either silencing PpeTAC1 or overexpressing PpeTAC1.

BACKGROUND OF INVENTION

The spatial patterning or architecture of any given tree is ultimately a consequence of numerous developmental, genetic, and environmental factors (Barthélémy D. and Caraglio Y., 2007, *Ann Bot.* 99, 375-407). Over the last 40 years, the study of tree architecture has intensified as it is a critical parameter for both the management and aesthetics of our agriculture, forests, and residential landscapes. Two features that prominently contribute to tree architectural differences include the pattern of branching and the angle of branch growth (Tomlinson, P. B., 1978, London: Cambridge University Press, 197-202). Combined, these factors control the number of branches produced, their spacing, and their directional orientations.

Branch growth angle is not uniform and subject to substantial variation within any given tree. Yet in a broad sense, branch angle has been used to classify trees into architectural types that are influenced by various tropisms. These include pillar or columnar forms that have narrow branch angles, spreading types with wide branch angles, and weeping in which shoots grow downwards. Unlike the apical shoot, axillary shoots are not subject to strict gravitropic or phototropic control, allowing them to grow in a variety of directions irrespective of the gravity and light vectors. Most familiar tree canopy shapes display a phenomenon whereby shoots closer to the apical meristem grow more vertical while those lower in the canopy tend to grow more horizontally.

Optimizing tree architecture to maximize productivity and simplify management is a chief goal of numerous tree crop industries. Thus tree architecture has been long studied with regard to horticultural practices associated with orchard and plantation forestry management. Tree growth responses to various types of pruning, hormone treatments, fertilizer applications, and effects of rootstock-scion interactions are well established. Architectural tree types suited for high density production systems and/or improved mechanization offer great promise for improving tree-based agricultural systems. In this regard, vertical or columnar tree forms are being investigated due to their erect axillary branch angles and reduced canopy diameter (Kelsey, D. F. and Brown, S. K., 1992, Fruit Var. J. 46, 83-87; Scorza et al., 1989, *J. Am. Soc. Hortic. Sci.* 114, 98-100). Considering the importance of canopy spatial patterning to the evolution and niche exploitation of land plants, little is known of the genes underlying the genetic basis of these traits.

Peach trees with extreme vertical branching resulting in a fastigiated tree shape have been developed for use in high density production systems (Miller and Scorza, 2010, *J. Amer. Pomological Soc.* 64, 199-217). This trait was initially referred to as "broomy" (br) (Yamazaki et al., 1987, New broomy flowering peach cultivars Terutebeni, Terutemomo, and Teruteshiro. *Bulletin of the Kanagawa Horticultural Experiment Station*, No. 34) and was later designated "pillar" inasmuch as it was shown to be incompletely dominant as heterozygous individuals have intermediate branch angles referred to as "upright" (Scorza et al., 1989, *J. Am. Soc. Hortic. Sci.* 114, 98-100; Tworkoski and Scorza, 2001, *J. Amer. Hort. Sci.* 126, 785-790; and Scorza et al., 2002, *J. Amer. Soc. Hort. Sci.* 127(2), 254-261). Axillary shoots in vertical trees tend to grow vertically regardless of their canopy position. Given the growing need to control canopy special patterns in trees, especially trees planted in nursery and orchards settings, there is a need to develop breeding and identification techniques to identify the genes responsible for different growth habits in tree varieties.

BRIEF SUMMARY OF THE INVENTION

Disclosed herein is an isolated polynucleotide sequence comprising polynucleotide sequence SEQ. ID. NO.: 1, wherein the polynucleotide sequence expression results in a plant having a horizontal phenotype characterized by axillary shoots having an increased horizontal orientation. In another embodiment of the invention, disclosed is a kit for the detection of a horizontal phenotype for a plant or germplasm, the kit comprising a reagent for the detection for the presence of SEQ. ID. NO.: 1.

Disclosed herein is an isolated polynucleotide sequence comprising polynucleotide sequence having 99% homology with SEQ. ID. NO.: 1, wherein the polynucleotide sequence expression results in a plant having a horizontal phenotype characterized by axillary shoots having an increased horizontal orientation.

Also disclosed is a method for controlling plant horizontal orientation, the method comprising overexpressing SEQ. ID. NO.: 1 in germplasm or plant wherein the overexpression of SEQ. ID. NO.: 1 result in a horizontal phenotype characterized by axillary shoots having an increased horizontal orientation. In one embodiment of the invention, the germplasm or plant being controlled is a *Prunus* cultivar. In another embodiment of the invention, the germplasm or plant being controlled is *Prunus persica*. In yet another embodiment of the invention, the germplasm or plant being controlled is *Prunus domestica*. In another embodiment of the invention is a transgenic *Prunus* cell or tissue prepared according to the disclosed method for controlling plant horizontal orientation. In another embodiment of the invention is a *Prunus* plant generated from the disclosed transgenic *Prunus* cell or tissue prepared according to the disclosed method for controlling plant horizontal orientation. In yet another embodiment of the invention is transgenic seed produced by the *Prunus* plant prepared according to the disclosed method for controlling plant horizontal orientation.

Also disclosed is a method for controlling plant horizontal orientation, the method comprising overexpressing a sequence having 99% homology with SEQ. ID. NO.: 1 in germplasm or plant wherein the overexpression of the sequence results in a horizontal phenotype characterized by axillary shoots having an increased horizontal orientation. In one embodiment of the invention, the germplasm or plant being controlled is a *Prunus* cultivar. In another embodiment of the invention is a transgenic *Prunus* cell or tissue prepared according to the disclosed method for controlling plant horizontal orientation. In another embodiment of the invention is a *Prunus* plant generated from the disclosed transgenic *Prunus* cell or tissue prepared according to the disclosed method for controlling plant horizontal orientation. In yet another embodiment of the invention is transgenic seed produced by the *Prunus* plant prepared according to the disclosed method for controlling plant horizontal orientation.

Also disclosed is a method for controlling plant branch vertical orientation, the method comprising silencing the expression of SEQ. ID. NO.: 1 in germplasm or plant, wherein the silencing of SEQ. ID. NO.: 1 result in a vertical phenotype characterized by axillary shoots having an increased vertical orientation. In one embodiment of the invention, the germplasm or plant being controlled is a *Prunus* cultivar. In another embodiment of the invention, the germplasm or plant being controlled is *Prunus persica*. In yet another embodiment of the invention, the germplasm or plant being controlled is *Prunus domestica*. In another embodiment of the invention is a transgenic *Prunus* cell or tissue prepared according to the disclosed method for controlling plant vertical orientation. In another embodiment of the invention is a *Prunus* plant generated from the disclosed transgenic *Prunus* cell or tissue prepared according to the disclosed method for controlling plant vertical orientation. In yet another embodiment of the invention is transgenic seed produced by the *Prunus* plant prepared according to the disclosed method for controlling plant vertical orientation.

Also disclosed is a method for controlling plant branch vertical orientation, the method comprising silencing the expression of a sequence having 99% homology with SEQ. ID. NO.: 1 in germplasm or plant, wherein the silencing of the sequence results in a vertical phenotype characterized by axillary shoots having an increased vertical orientation. In one embodiment of the invention, the germplasm or plant being controlled is a *Prunus* cultivar. In another embodiment of the invention is a transgenic *Prunus* cell or tissue prepared according to the disclosed method for controlling plant vertical orientation. In another embodiment of the invention is a *Prunus* plant generated from the disclosed transgenic *Prunus* cell or tissue prepared according to the disclosed method for controlling plant vertical orientation. In yet another embodiment of the invention is transgenic seed produced by the *Prunus* plant prepared according to the disclosed method for controlling plant vertical orientation.

BRIEF DESCRIPTION OF THE DRAWINGS

The present invention together with the disclosed embodiments may best be understood from the following detailed description of the drawings, wherein.

BRIEF DESCRIPTION OF THE SEQUENCES

Figure 1A:
FIGS. 1A, 1B, and 1C depict two year old *Prunus persica* trees from an F2 segregating population standard, upright, and vertical phenotypes, respectively.
Figure 1B:
Figure 1C:

SEQ. ID. NO. 1:
atgaagatcttcaactgggttcataagaggcttcatcaaagggtcgtc aaggatgggtttgctgggaatgtgaaaaagagtgaactggaaaccaat gacaaggacacacaagcatttctcaaacaagttggccttgttaatgtg gatgggcttgatggttggagggatggcattttaactataggcaccttt ggtttcgacccctaaaaccctctacccaccaaaacgaatatttcgtt ctggagagcgaagaagacgatcaggaaagccatggattttcacacagt ggtaatgatgatgatgatgatgatgatgaacattatgatcatagtgtt gaagatgaagaactgaaccctttaatgtttacaacatttgaacacagc tttgaggatattgggtcaaattttgatgccattgttcagaaaccagct gatgtgatcctgaccgttgatggtgtccctcttactccatttgagggg -continued
tccagtgaaatcagtactaaacctgatcagagtgctaatgatcagagc aagaataagaaaggtcagagaattacactggctgacttgttccaggct gatgttcctgatgttggtcaactgaagcttgactctggcaaggtccag ccagaaatggagaaaaaaatgaatgccagaacaaggagtggcctagca tttgccaagaaactcatccctcgcgtcaaagatgattcaagtccaatc aaaaatatgcaacgactgatgaggaggatgttgaagaggaagatccat ccagctgagcttgaagtcaagattcacaaatcagatggccagaagcag cccagtgcggtagagctcatctccaatgtcgaaaatgatgcttatgaa tcggtttctttgcttccaattcaaggtgcccttgtgtgcactga
is the cDNA sequence of PpeTAC1.

SEQ. ID. NO. 2: TGAACCACTTGTGCTTCTGCGA is a 5'→3' primer used in expression analysis of PpeTAC1.

SEQ. ID. NO. 3: ATTCAAACAGCAGCCACAACGG is a 5'→3' primer used in expression analysis of PpeTAC1.

SEQ. ID. NO. 4: GGAAATGCAAATAGGGAATTGG is a 5'→3' primer used in expression analysis of PpeTAC1.

SEQ. ID. NO. 5: CTCTCTCTCTGTGGATTAAA is a 5'→3' primer used in expression analysis of PpeTAC1.

SEQ. ID. NO. 6: CTCACATGGCCATAGGGATAGT is a 5'→3' primer used in expression analysis of PpeTAC1.

SEQ. ID. NO. 7: TGAAAGACGTACGCCAAGCCAA is a 5'→3' primer used in expression analysis of PpeTAC1.

SEQ. ID. NO. 8: AGAGCGAAGAAGACGATCAGGA is a 5'→3' primer used in expression analysis of PpeTAC1.

SEQ. ID. NO. 9: CAGCTGGTTTCTGAACAATGGC is a 5'→3' primer used in expression analysis of PpeTAC1.

SEQ. ID. NO. 10: AAGCACACGTTCCACTCTGT is a 5'→3' primer used in expression analysis of PpeTAC1.

SEQ. ID. NO. 11: GGCAATAGTTGTGTGAGGT-GAGGT is a 5'→3' primer used in expression analysis of PpeTAC1.

SEQ. ID. NO. 12: ACAGCTAAGCTCCTACTTCAACCC is a 5'→3' primer used in expression analysis of PpeTAC1.

SEQ. ID. NO. 13: AGAGAGTGGCTTTGCTTGGTCT is a 5'→3' primer used in expression analysis of PpeTAC1.

SEQ. ID. NO. 14: TCTTCCATCTAAGCTGCCACAT is a 5'→3' primer used in expression analysis of PpeTAC1.

SEQ. ID. NO. 15: GCAGTGAATTGAA-GAAATAATCGTCG is a 5'→3' primer used in expression analysis of PpeTAC1.

SEQ. ID. NO. 16: GAATTCAATTGCTCACAAAATAT-GAAG is a 5'→3' primer used in expression analysis of full length PpeTAC1.

SEQ. ID. NO. 17: GGATCCTTAATTCAGTGCACACAA is a 5'→3' primer used in expression analysis of PpeTAC1.

SEQ. ID. NO. 18: TTTGCCAAGAAACTCATCCCTCGC is a 5'→3' primer used in expression analysis of PpeTAC1.

SEQ. ID. NO. 19: GCTGCTTCTGGCCATCTGATTTGT is a 5'→3' primer used in expression analysis of PpeTAC1.

SEQ. ID. NO. 20: AATTGCTCACAAAATATGAAG is a forward primer used to detect SEQ. ID. NO. 1.

SEQ. ID. NO. 21: TTAATTCAGTGCACACAA is a reverse primer used to detect SEQ. ID. NO. 1.

SEQ. ID. NO. 22: TGGGTTTGCTGGGAATGTGA is a forward primer used to assemble a PpeTAC1 silencing construct in a plum species.

SEQ. ID. NO. 23: CAGCTGGTTTCTGAACAATGGC is a reverse primer used to assemble a PpeTAC1 silencing construct in a plum species.

SEQ. ID. NO. 24:
TGGGTTTGCTGGGAATGTGAAAAAGAGTGAACTGGAAACCAATGACAAGG

ACACACAAGCATTTCTCAAACAAGTTGGCCTTGTTAATGTGGATGGGCTT

GATGGTTGGAGGGATGGCATTTTAACTATAGGCACCTTTGGTTTCGACCC

CCTAAAACCCTCTACCCACCAAAACGAATATTTCGTTCTGGAGAGCGAAG

AAGACGATCAGGAAAGCCATGGATTTTCACACAGTGGTAATGATGATGAT

GATGATGATGATGAACATTATGATCATAGTGTTGAAGATGAAGAACTGAA

CCCTTTAATGTTTACAACATTTGAACACAGCTTTGAGGATATTGGGTCAA

ATTTTGATGCCATTGTTCAGAAACCAGCTG is a PpeTAC1 silencing construct.

SEQ. ID. NO: 25: GAATTCAATTCGCTCACAAAATAT-GAAG is a primer used to amplify full length PpeTAC1.

SEQ. ID. NO: 26: CCTTGTGTGCACTGAATTAAG-GATCC is a reverse primer used to amplify full length PpeTAC1.

DETAILED DESCRIPTION OF THE INVENTION

Disclosed here is an isolated polynucleotide sequence comprising polynucleotide sequence SEQ. ID. NO.: 1, and referred to as PpeTAC1, wherein the polynucleotide sequence expression results in a tree having a spreading phenotype characterized by axillary shoots having an increased horizontal orientation.

Definitions

Unless otherwise defined, all technical and scientific terms used herein have the same meaning as commonly understood by one of ordinary skill in the art to which the presently disclosed subject matter pertains. For clarity of the present specification, certain definitions are presented herein below.

As used herein, the term "shoot" refers to the aerial portion of a plant that includes the stem, leaves, axillary meristems, and apical meristems.

As used herein, the term "axillary shoot" refers to either a shoot originating from the axil of leaf or from an axillary bud.

The term "gene" refers to a DNA sequence involved in producing a polypeptide or precursor thereof. The polypeptide can be encoded by a full-length coding sequence or by any portion of the coding sequence, such as exon sequences.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)). Methods commonly employed to determine identity between sequences include, for example, those disclosed in Carillo, H., and Lipman, D., *SIAM J. Applied Math*. (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, the term "recombinant DNA construct" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

A nucleic acid sequence can be inserted into a vector by a variety of procedures. In general, the sequence is ligated to the desired position in a vector following digestion of the insert and the vector with appropriate restriction endonucleases. Alternatively, blunt ends in both the insert and the vector may be ligated. A variety of cloning techniques are known in the art, e.g., as described in Sambrook, J. et al., Molecular Cloning, A Laboratory Manual, Cold Spring Harbor Press, Plainview, N.Y., (1989) and Ausubel, F. M. et al., Current Protocols in Molecular Biology, John Wiley & Sons, New York, N.Y. (1989). Such procedures and others are deemed to be within the scope of those skilled in the art.

The vector can be in the form of a plasmid, a viral particle, or a phage. Preferably, as disclosed herein the vector is a bacterial vector. Other vectors include chromosomal, non-chromosomal and synthetic DNA sequences, pET-30a and derivatives of pET-30; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook, T. et al., Molecular Cloning: A Laboratory Manual, Cold Spring Harbor Press, Plainview, N.Y., (1989).

"Small interfering RNA" or "siRNA" refers to a short double-strand of ribonucleic acid, approximately 18 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

As used herein, "knock-down" is defined as the act of binding an oligonucleotide with a complementary nucleotide sequence of a gene as such that the expression of the gene or mRNA transcript decreases. In an embodiment, knock-down of a PpeTAC1 gene in a transgenic plant confers control of branching for said transgenic plant.

dsRNA containing a nucleotide sequence complementary to PpeTAC1 gene. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for plant resistance to RNA viruses. Thus, sequence identity may be optimized by sequence comparison and alignment algorithms known in the art. Thus, the determination of percent identity between any two sequences can be accomplished using a mathematical algorithm. Non-limiting examples of such mathematical algorithms are the algorithm of Myers and Miller (1988. CABIOS 4: 11-17), the local homology algorithm of Smith et al. (1981. Adv. Appl. Math. 2: 482); the homology alignment algorithm of Needleman and Wunsch (1970. J. Mol. Biol. 48: 443-453); the search-for-similarity-method of Pearson and Lipman (1988. Proc. Natl. Acad. Sci. 85: 2444-2448; the algorithm of Karlin and Altschul (1990. Proc. Natl. Acad. Sci. USA 87: 2264), modified as in Karlin and Altschul (1993. Proc. Natl. Acad. Sci. USA 90: 5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the Align program (Version 2.0 (Invitrogen, Carlsbad, Calif.); and GAP, BESTFIT, BLAST®, FASTA, and TFASTA in the Wisconsin Genetics Software Package, Version 8 (available from Genetics Computer Group (GCG), 575 Science Drive, Madison, Wis., USA); Multiple Alignment tool, CLC Genomics Workbench, Version 6.1 (available from CLC Bio, 10 Rogers Street #101, Cambridge, Mass.). Alignments using these programs can be performed using the default parameters. The CLUSTAL program is well described by Higgins et al. 1988. *Gene* 73:237-244; Higgins et al. 1989. *CABIOS* 5:151-153; Corpet et al. 1988. *Nucleic Acids Res.* 16:10881-90; Huang et al. 1992. *CABIOS* 8:155-65; and Pearson et al. 1994. *Meth. Mol. Biol.* 24:307-331. The BLAST® programs of Altschul et al. 1990. *J. Mol. Biol.* 215; 403-410 are based on the algorithm of Karlin and Altschul (1990), supra.

Greater than 90% sequence identity, or even 100% sequence identity, between the inhibitory RNA and the portion of the eukaryotic translation initiation factor target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 18, 19, 21, 22, 23, or 24 bases. In a preferred embodiment, the length of the double-stranded nucleotide sequence is approximately from about 21 to about 24 nucleotides in length for plants.

The dsRNA construct disclosed herein may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell.

While the examples provided wherein describe dsRNA constructs that target the branching angle of a plum and peach tree, it is contemplated that when read in conjunction with the teaching disclosed herein, the construction of other dsRNA constructs targeting PpeTAC1 in a plurality of trees and cultivars such as *Prunus domesitac* (European plum), *Prunus persica* (peach), *Prunus armeniaca* (apricot), *Prunus salicina* (Japanese plum), *Prunus mume* (Chinese plum), *Prunus amygdalus*, (almond), *Prunus avium* (sweet cherry), and *Prunus cerasus* (sour cherry).

*Agrobacterium*-Mediated Transformation

*Agrobacterium*-mediated gene transfer exploits the natural ability of *Agrobacterium* to transfer DNA into plant chromosomes. As is well known in the art, *Agrobacterium* is a plant pathogen that can transfer a set of genes into plant cells. In some embodiments of the presently disclosed subject matter, immature *Prunus* cells can be transformed using *Agrobacterium tumefaciens*.

Those skilled in the art will appreciate that the disclosed methods apply equally well to *Agrobacterium rhizogenes*. Transformation using *Agrobacterium rhizogenes* has developed analogously to that of *Agrobacterium tumefaciens* and has been successfully utilized to transform plants, including but not limited to, alfalfa, *Solarium nigrum* L., and poplar. See, for example, Hooykaas, *Plant Mol. Biol.* (1989) 13: 327; Smith et al. *Crop Science* (1995) 35: 301 (1995); Chilton, *Proc. Natl. Acad. Sci. USA* (1993) 90: 3119; Mollony et al. *Monograph Theor. Appl. Genet NY* (1993) 19: 148; Ishida et al. *Nature Biotechnol.* (1996) 14: 745 (1996); and Komari et al. *The Plant Journal* (1996) 10:165 (1996), the disclosures of which are incorporated herein by reference.

For *Agrobacterium*-mediated gene transfer, wounding of the explant tissue can be used to facilitate gene transfer. Accordingly, in some embodiments, a wound can be created in the explant tissue. The *Agrobacterium*-mediated transformation process of the presently disclosed subject matter can comprise several steps. The basic steps can include, but are not limited to, an infection step and a co-cultivation step. In some embodiments, these steps are followed by a selection step, and in some embodiments, by a selection and a regeneration step, as discussed in detail herein below.

In the infection step, plant cells to be transformed are exposed to *Agrobacterium*. In some embodiments, the cells are brought into contact with the *Agrobacterium* in a liquid medium. Alternatively, in some embodiments, the cells are brought into contact with the *Agrobacterium* in a solid medium. In some embodiments, the *Agrobacterium* can be modified to contain a gene or nucleic acid of interest, wherein the nucleic acid can be inserted into a genetic construct, which can comprise a plasmid or other suitable vector.

A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. Methods for Plant Molecular Biology, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally regulated, or cell- or tissue-specific expression), a transcription initiation start site, a ribosome binding site, an RNA processing signal, a transcription termination site, and/or a polyadenylation signal.

The term "promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue specificity of a promoter, for example, is exemplified by the promoter sequence which specifically induces gene expression in plant tissues including vegetative buds, stems, vascular tissues, apical meristems, lateral meristems, roots, root meristems, fruit and flower buds. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg, 1989, *Biochemistry of Plants* 15:1-82. It is further recognized that since in most cases the exact boundaries of regulatory sequences have not been completely defined, nucleic acid fragments of different lengths may have identical promoter activity.

As used herein, the term "horizontal orientation" refers to the overall branch orientation of a plant.

As used herein, the term "vertical orientation" in reference to a plant refers to the branch orientation of a plant. To the extent that a plant or tree is referenced to have a "pillar" orientation in the art, as used herein, said plant or tree is referred to having a "vertical orientation".

In an embodiment of the invention, targeted cleavage events can be used, for example, to induce targeted mutagenesis, induce targeted deletions of cellular DNA sequences, and facilitate targeted recombination and integration at a predetermined chromosomal ppTAC or ppeTAC locus. Techniques of nucleotide editing can be found for example, Urnov et al. (2010) Nature 435(7042):646-51; United States Patent Publications 20030232410; 20050208489; 20050026157; 20050064474; 20060188987; 20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) Proc. Natl. Acad. Sci. USA 104(9):3055-3060 describes using designed ZFNs for targeted gene addition at a specified locus. U.S. Patent Publication 20110041195 describes methods of making homozygous diploid organisms.

For example, a ppTAC or ppeTAC-specific DNA recognition and cleavage protein may be, for example and without limitation, a ZFN; a TALEN; RNA-guided CRISPR-Cas9, a recombinase (e.g., Cre, Hin, RecA, Tre, and FLP recombinases); a meganuclease, and an engineered protein derived from any of the foregoing or their equivalents. Cleavage may also be effected using the CRISPR/Cas system with an engineered crRNA/tracr RNA (single guide RNA) to guide specific cleavage.

The following Examples have been included to illustrate representative and exemplary modes of the presently disclosed subject matter. In light of the present disclosure and the general level of skill in the art, those of skill will appreciate that the following Examples are intended to be exemplary only and that numerous changes, modifications, and alterations can be employed without departing from the spirit and scope of the presently disclosed subject matter.

Example 1

Sequence-Based Mapping of Br Using Pnomes

Figure 2:
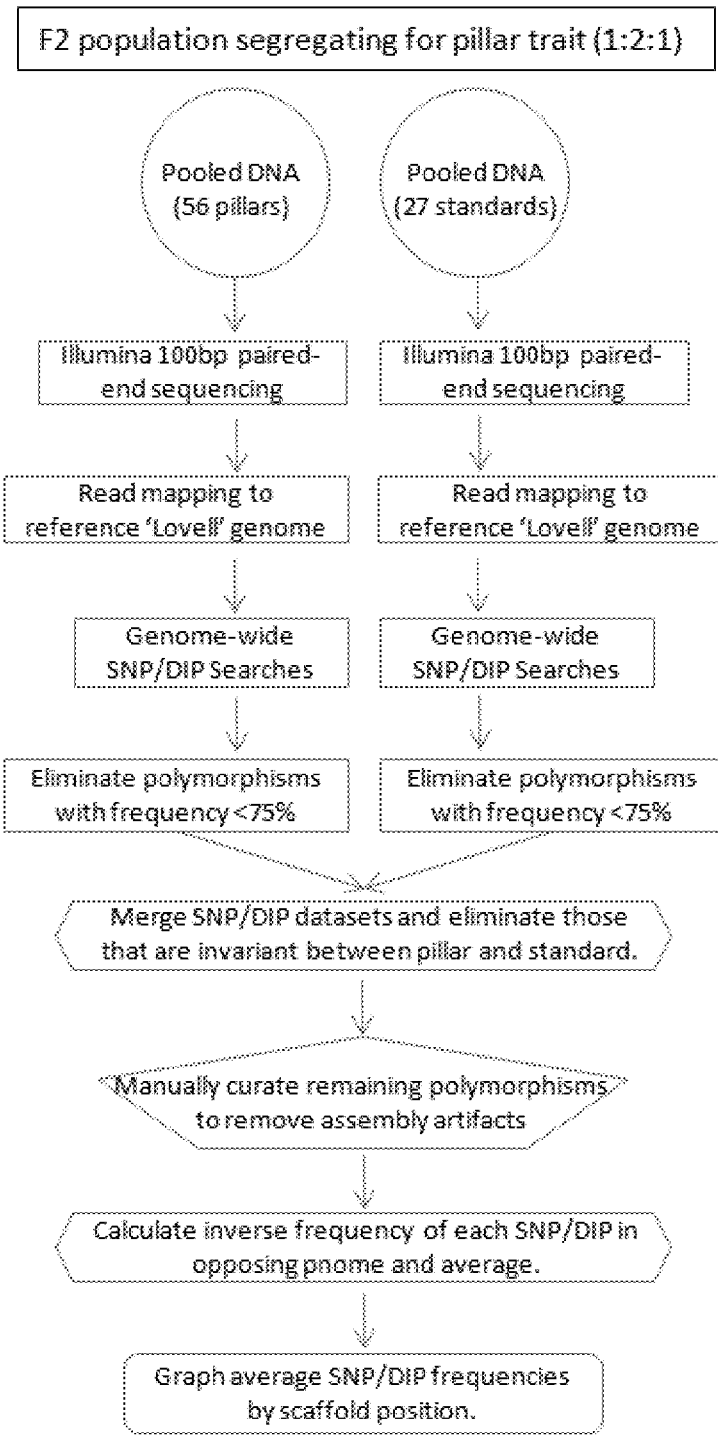
FIG. 2 is a general schematic to identify the polymorphism responsible for the vertical trait from peach tree populations.

To identify the polymorphism responsible for the vertical trait from peach tree populations. A strategy for simultaneous genetic mapping and candidate gene identification using next-generation sequencing of pooled genomes, dubbed "pnomes" was utilized. The pnomes strategy is based on sequencing a population(s) of segregating individuals pooled by a specific trait(s). In theory, the linkage of individual polymorphisms to a trait of interest should be measurable by calculating the abundance of each polymorphism within a given pnome assembled against a reference genome. Tightly linked polymorphisms should occur at high frequency in the pnome containing the trait while those same polymorphisms should be rare or absent in the pnome lacking the trait, and vice versa. Consequently, when graphed by nucleotide position, the data should produce a bell-shaped curve delineating the location of the trait. A schematic describing the pnome strategy is depicted in FIG. 2. To test the efficacy of the pnomes strategy, DNA was extracted from 27 standard stature trees and 56 vertical individuals derived from an F2 segregating population.

Peach Tree Populations

Two sources of br were used in this study. "Italian Pillar" was obtained as pollen from the Instituto Sperimentale per la Frutticoltura, Forli, Italy. "New Jersey Pillar" represented a different source of the br gene and was obtained from Japan through Rutgers University (Scorza, R., Bassi, D. and Liverani, A., 2002, *J. Amer. Soc. Hort. Sci.* 127(2), 254-261. While both sources of br expressed the vertical growth habit they differed in flower and fruit characteristics (Id). For pnome mapping, an F2 peach (*Prunus persica*) population of over 200 individuals segregating for the vertical trait was used. This was derived from selfing an F1 individual which was a progeny of an F0 cross between the vertical cultivar 'Crimson Rocket' and the doubled haploid variety 'True Gold' that has a standard architecture. 'Crimson Rocket' was derived from "Italian Pillar" germplasm (http://ddr.nal.usda.gov/bitstream/10113/12968/1/IND44038654.pdf). The trees were phenotyped and leaf tissue was collected from select 4 year old trees in which the vertical and standard phenotypes were most apparent. Fine mapping was performed using trees from several different segregating populations in which the vertical trait was derived from 'Italian Pillar'. From these, 157 vertical trees were chosen based on their having a clear vertical phenotype. Standard and upright individuals were not used for fine mapping due to the inability to accurately phenotype them.

These DNAs were subsequently combined into two pools (standard and vertical) for pnome sequencing. Genomic DNA was extracted from liquid nitrogen treated ground leaf samples with the E.Z.N.A.™ High Performance (HP) DNA Kit (Omega Bio-Tek Inc. http://www.omegabiotek.com). Modifications to the Frozen Specimens protocol were the addition of 2% PVP-40 (w/v) to Buffer CPL and the optional addition of 2-mercaptoethanol. The fluorescent dye, PicoGreen was used to obtain a more specific double stranded DNA measurement utilizing the Quant-iT PicoGreen kit (Molecular Probes, Inc., Eugene, Oreg.). The reactions were set up according to the manufacturer's directions with each 100 ul reaction containing 40-400 ng of leaf DNA as determined by Nanodrop spectrophotometer readings. A second set of reactions was set up with 0.1× leaf DNA. Standard curves were run simultaneously that ranged from 0 to 250 ng of lambda DNA included in the kit. All reactions were run in duplicate in a 96 well microtiter plate. The reactions were allowed to proceed for 5 min in the dark and were then read utilizing a Cytofluor 4000/TR (Applied Biosystems, Inc., Foster City, Calif.). Standard curves were constructed from the lambda DNA readings and the leaf DNA concentrations were obtained from the curves. The readings ranged from 18% to 72% of the Nanodrop readings. Those Resulting DNA samples were combined in equal molar ratios to generate the vertical and standard pools for pnome sequencing.

The two DNA pools were sequenced via Illumina 100 bp paired-end reads to an estimated coverage of 2× and 1.6× (relative to the number of genomes in each pnome), respectively. Next, the vertical and standard reads were separately assembled against the peach genome [Sosinski et al., in preparation; sequence available at Retrieved from the Internet: rosaceae.org/peach/genome] using CLC Genomics Workbench Software (CLC Bio, Aarhus, Denmark). Default parameters were used and non-specific reads were excluded from mapping. SNPs and DIPS were identified from each pnome assembly using the respective CLC tools. Default parameters for SNP/DIP significance were changed as follows: minimum coverage and paired coverage set to 20, maximum coverage set to 500, minimum variant count required set to 20, maximum expected variations set to 2. SNP/DIP frequency is automatically calculated by the software based on the number of high quality reads in which each polymorphism occurs relative to the total number of high quality reads that span that nucleotide position. To compare the vertical vs. standard SNP/DIP datasets, they were each filtered to remove invariant SNPs/DIPs, unlinked SNPs/DIPs, and artifacts arising from assembly errors. Filtering was performed as follows: 1) SNPs/DIPs with the same variant allele (relative to the reference) occurring at a frequency >75% in both the vertical and standard pnomes were removed. These largely represent non-segregating polymorphisms that only occur relative to Lovell genome. 2) SNP/DIPs with a variant frequency below 75% were removed from each dataset to eliminate unlinked polymorphisms. 3) The remaining SNPs and DIPs were manually verified by inspection of the corresponding sequence assemblies to eliminate artifacts arising from assembly differences.

To create an allele frequency map, the frequency of all SNPs/DIPs in the pnome from which they were absent or at low abundance was calculated. Next, the inverse frequencies from the opposing pnome were calculated. The datasets were filtered again based on the frequency scores of the inverse pnome (removed if less than 75%). The two frequencies were then averaged to get a single frequency value. This additional step captures segregation data for all SNPs/DIPs in both pnomes providing a more robust frequency estimate. The resulting average SNP/DIP frequencies were graphed by reference nucleotide position to generate the allele frequency map. After mapping, a low threshold SNP/DIP search was done within the mapped region to identify those that may have been missed during the initial, more stringent searches. The low stringency search parameters used were: minimum coverage and paired coverage set to 10, maximum coverage set to 500, minimum variant count required set to 10, maximum expected variations set to 2. This additional step only captured 3 polymorphisms which had been excluded by the initial more stringent searches in Table 1.

TABLE 1

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Standard | 963617 | SNP | A | T | 25 | 32 | | 78.1% | 80.0% | 79.1% |
| Standard | 963625 | SNP | C | G | 25 | 33 | | 75.8% | 80.5% | 78.2% |
| Standard | 2482935 | SNP | G | A | 45 | 59 | | 76.3% | 79.5% | 77.9% |
| Standard | 2482955 | SNP | T | C | 48 | 61 | | 78.7% | 84.8% | 81.8% |
| Standard | 2509017 | SNP | G | A | 26 | 34 | | 76.5% | 82.7% | 79.6% |
| Standard | 2618064 | SNP | A | G | 38 | 50 | | 76.0% | 78.8% | 77.4% |
| Pillar | 2766475 | DIP | — | A | 61 | 78 | | 78.2% | 78.2% | 78.2% |
| Pillar | 2955393 | SNP | C | T | 42 | 55 | | 76.4% | 75.0% | 75.7% |
| Pillar | 3032678 | SNP | T | C | 47 | 62 | | 75.8% | 79.6% | 77.7% |
| Pillar | 3033011 | SNP | T | C | 54 | 71 | Val19Ala | 76.1% | 78.4% | 77.3% |
| Pillar | 3036697 | SNP | A | C | 48 | 62 | | 77.4% | 84.4% | 80.9% |
| Pillar | 3052886 | SNP | T | C | 34 | 39 | | 87.2% | 78.1% | 82.7% |
| Pillar | 3080100 | SNP | T | G | 30 | 37 | | 81.1% | 86.8% | 84.0% |
| Pillar | 3085288 | SNP | G | A | 30 | 39 | | 76.9% | 80.0% | 78.5% |
| Pillar | 3085301 | SNP | G | A | 33 | 44 | | 75.0% | 81.8% | 78.4% |
| Pillar | 3085305 | SNP | C | G | 33 | 44 | | 75.0% | 81.8% | 78.4% |
| Pillar | 3085611 | SNP | G | A | 35 | 45 | | 77.8% | 77.5% | 77.7% |
| Pillar | 3092355 | SNP | C | G | 30 | 39 | | 76.9% | 82.8% | 79.9% |
| Pillar | 3092369 | SNP | G | A | 33 | 42 | | 78.6% | 77.8% | 78.2% |
| Pillar | 3098176 | SNP | T | A | 21 | 27 | | 77.8% | 78.6% | 78.2% |
| Pillar | 3100549 | SNP | G | C | 43 | 55 | | 78.2% | 75.0% | 76.6% |
| Pillar | 3144488 | SNP | T | C | 38 | 44 | | 86.4% | 77.6% | 82.0% |
| Pillar | 3144743 | SNP | G | T | 37 | 48 | | 77.1% | 81.8% | 79.5% |
| Pillar | 3144760 | SNP | C | T | 39 | 49 | | 79.6% | 84.0% | 81.8% |
| Pillar | 3147195 | SNP | T | G | 34 | 45 | | 75.6% | 82.5% | 79.1% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Pillar | 3149672 | DIP | C | — | 34 | 39 | | 87.2% | 75.9% | 81.6% |
| Pillar | 3150679 | SNP | G | A | 53 | 68 | | 77.9% | 76.7% | 77.3% |
| Pillar | 3166695 | SNP | G | A | 44 | 54 | | 81.5% | 75.6% | 78.6% |
| Pillar | 3166696 | SNP | T | A | 44 | 54 | | 81.5% | 75.6% | 78.6% |
| Pillar | 3166698 | SNP | A | G | 43 | 53 | | 81.1% | 75.6% | 78.4% |
| Pillar | 3166948 | SNP | T | A | 38 | 47 | | 80.9% | 76.5% | 78.7% |
| Pillar | 3167028 | SNP | C | A | 35 | 42 | | 83.3% | 85.4% | 84.4% |
| Pillar | 3180416 | SNP | T | G | 25 | 32 | | 78.1% | 77.1% | 77.6% |
| Pillar | 3180424 | SNP | T | C | 21 | 27 | | 77.8% | 78.4% | 78.1% |
| Pillar | 3241551 | SNP | A | G | 25 | 30 | | 83.3% | 76.5% | 79.9% |
| Pillar | 3248377 | SNP | T | G | 49 | 64 | | 76.6% | 80.0% | 78.3% |
| Pillar | 3248714 | SNP | T | A | 56 | 72 | | 77.8% | 75.9% | 76.9% |
| Pillar | 3257705 | SNP | T | A | 48 | 62 | | 77.4% | 77.6% | 77.5% |
| Pillar | 3267865 | SNP | C | A | 49 | 65 | | 75.4% | 75.3% | 75.4% |
| Pillar | 3268136 | SNP | C | T | 72 | 96 | | 75.0% | 77.0% | 76.0% |
| Pillar | 3273918 | SNP | T | C | 49 | 64 | | 76.6% | 75.0% | 75.8% |
| Pillar | 3273937 | SNP | G | C | 58 | 73 | | 79.5% | 77.6% | 78.6% |
| Pillar | 3293060 | SNP | G | T | 34 | 42 | | 81.0% | 79.4% | 80.2% |
| Pillar | 3311512 | SNP | T | C | 40 | 52 | | 76.9% | 75.0% | 76.0% |
| Pillar | 3311843 | SNP | C | A | 36 | 41 | Leu682Ile | 87.8% | 80.6% | 84.2% |
| Pillar | 3311861 | SNP | C | G | 35 | 40 | Leu688Val | 87.5% | 81.8% | 84.7% |
| Pillar | 3313743 | SNP | T | C | 66 | 88 | | 75.0% | 75.7% | 75.4% |
| Pillar | 3313957 | SNP | A | T | 57 | 75 | | 76.0% | 75.5% | 75.8% |
| Pillar | 3313961 | SNP | T | A | 58 | 77 | | 75.3% | 76.0% | 75.7% |
| Pillar | 3356896 | SNP | A | G | 28 | 37 | | 75.7% | 84.2% | 80.0% |
| Pillar | 3364958 | SNP | A | T | 23 | 29 | | 79.3% | 75.0% | 77.2% |
| Pillar | 3401921 | SNP | T | A | 41 | 51 | | 80.4% | 77.1% | 78.8% |
| Pillar | 3401926 | SNP | C | G | 40 | 51 | | 78.4% | 77.1% | 77.8% |
| Pillar | 3406324 | SNP | A | C | 24 | 32 | | 75.0% | 77.3% | 76.2% |
| Pillar | 3443262 | SNP | G | A | 27 | 36 | | 75.0% | 76.0% | 75.5% |
| Pillar | 3461242 | SNP | T | C | 58 | 76 | | 76.3% | 75.0% | 75.7% |
| Pillar | 3462660 | SNP | T | C | 32 | 42 | | 76.2% | 78.4% | 77.3% |
| Pillar | 3462665 | SNP | T | G | 33 | 43 | | 76.7% | 75.7% | 76.2% |
| Pillar | 3484550 | SNP | T | C | 46 | 57 | | 80.7% | 76.0% | 78.4% |
| Pillar | 3484781 | SNP | A | G | 37 | 47 | | 78.7% | 76.9% | 77.8% |
| Pillar | 3600327 | SNP | T | C | 32 | 39 | | 82.1% | 75.3% | 78.7% |
| Pillar | 3601121 | SNP | A | T | 36 | 46 | | 78.3% | 80.0% | 79.2% |
| Pillar | 3601670 | SNP | G | A | 46 | 61 | | 75.4% | 75.0% | 75.2% |
| Pillar | 3622206 | SNP | T | G | 30 | 40 | | 75.0% | 76.3% | 75.7% |
| Pillar | 3625503 | SNP | T | G | 50 | 66 | | 75.8% | 82.4% | 79.1% |
| Pillar | 3625511 | SNP | T | C | 54 | 70 | | 77.1% | 82.0% | 79.6% |
| Pillar | 3630577 | SNP | A | T | 38 | 50 | | 76.0% | 78.4% | 77.2% |
| Pillar | 3761475 | SNP | T | C | 48 | 62 | | 77.4% | 77.8% | 77.6% |
| Pillar | 3761477 | SNP | C | T | 48 | 62 | | 77.4% | 78.2% | 77.8% |
| Pillar | 3762446 | SNP | G | C | 54 | 66 | | 81.8% | 76.0% | 78.9% |
| Pillar | 3763103 | SNP | A | T | 31 | 40 | | 77.5% | 77.0% | 77.3% |
| Pillar | 3767980 | SNP | C | T | 48 | 60 | | 80.0% | 76.8% | 78.4% |
| Pillar | 3773383 | SNP | T | G | 52 | 65 | | 80.0% | 75.9% | 78.0% |
| Pillar | 3775285 | SNP | T | C | 32 | 41 | | 78.0% | 78.8% | 78.4% |
| Pillar | 3808842 | SNP | G | C | 28 | 36 | | 77.8% | 78.7% | 78.3% |
| Pillar | 3808844 | SNP | T | C | 28 | 36 | | 77.8% | 78.3% | 78.1% |
| Pillar | 3808846 | SNP | G | A | 28 | 36 | | 77.8% | 79.6% | 78.7% |
| Pillar | 3810346 | SNP | T | C | 34 | 41 | | 82.9% | 81.8% | 82.4% |
| Pillar | 3810356 | SNP | C | T | 32 | 39 | | 82.1% | 81.8% | 82.0% |
| Pillar | 3926466 | SNP | G | A | 42 | 56 | | 75.0% | 77.3% | 76.2% |
| Pillar | 3930036 | SNP | A | G | 63 | 77 | | 81.8% | 79.6% | 80.7% |
| Pillar | 3962253 | SNP | A | G | 75 | 100 | | 75.0% | 76.6% | 75.8% |
| Pillar | 3963692 | SNP | C | T | 63 | 84 | | 75.0% | 82.0% | 78.5% |
| Pillar | 3975685 | SNP | A | G | 53 | 66 | | 80.3% | 89.0% | 84.7% |
| Pillar | 4007123 | SNP | T | G | 68 | 89 | | 76.4% | 75.0% | 75.7% |
| Pillar | 4007130 | SNP | G | T | 67 | 89 | | 75.3% | 77.8% | 76.6% |
| Pillar | 4007144 | SNP | C | A | 64 | 84 | | 76.2% | | 76.2% |
| Pillar | 4007390 | SNP | T | G | 44 | 56 | | 78.6% | 77.3% | 78.0% |
| Pillar | 4007894 | SNP | G | A | 45 | 56 | | 80.4% | 78.8% | 79.6% |
| Pillar | 4016938 | SNP | T | C | 41 | 53 | | 77.4% | 75.5% | 76.5% |
| Pillar | 4021171 | SNP | C | A | 35 | 45 | | 77.8% | 79.1% | 78.5% |
| Pillar | 4025194 | SNP | G | A | 59 | 69 | | 85.5% | 75.0% | 80.3% |
| Pillar | 4043564 | DIP | AA | — | 25 | 33 | | 75.8% | 84.6% | 80.2% |
| Pillar | 4043577 | SNP | C | T | 42 | 48 | | 87.5% | 84.6% | 86.1% |
| Pillar | 4043597 | SNP | C | A | 39 | 47 | | 83.0% | 84.6% | 83.8% |
| Pillar | 4043604 | SNP | G | A | 35 | 43 | | 81.4% | 88.0% | 84.7% |
| Pillar | 4043641 | SNP | C | T | 35 | 45 | | 77.8% | 77.3% | 77.6% |
| Pillar | 4043659 | SNP | G | A | 27 | 35 | | 77.1% | 76.7% | 76.9% |
| Pillar | 4043681 | SNP | T | C | 21 | 26 | | 80.8% | 81.5% | 81.2% |
| Pillar | 4043708 | SNP | G | T | 20 | 25 | | 80.0% | 88.9% | 84.5% |
| Pillar | 4043751 | SNP | C | T | 21 | 27 | | 77.8% | 82.4% | 80.1% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Pillar | 4043761 | SNP | C | T | 25 | 32 | | 78.1% | 81.8% | 80.0% |
| Pillar | 4043785 | SNP | A | G | 36 | 43 | | 83.7% | 81.5% | 82.6% |
| Pillar | 4076564 | SNP | T | C | 45 | 58 | | 77.6% | 77.3% | 77.5% |
| Pillar | 4076951 | SNP | A | G | 48 | 64 | | 75.0% | 80.9% | 78.0% |
| Pillar | 4130378 | SNP | A | G | 28 | 37 | | 75.7% | 78.0% | 76.9% |
| Pillar | 4131447 | DIP | C | — | 22 | 29 | | 75.9% | 78.6% | 77.3% |
| Pillar | 4131448 | SNP | A | T | 23 | 30 | | 76.7% | 79.5% | 78.1% |
| Pillar | 4133286 | SNP | G | A | 34 | 45 | | 75.6% | 75.0% | 75.3% |
| Pillar | 4235724 | SNP | T | C | 20 | 25 | | 80.0% | 84.8% | 82.4% |
| Pillar | 4235923 | SNP | G | A | 41 | 49 | | 83.7% | 80.0% | 81.9% |
| Pillar | 4235933 | SNP | A | C | 43 | 52 | | 82.7% | 75.0% | 78.9% |
| Pillar | 4236052 | SNP | C | G | 36 | 45 | | 80.0% | 75.5% | 77.8% |
| Pillar | 4309593 | SNP | A | G | 65 | 81 | | 80.2% | 80.8% | 80.5% |
| Pillar | 4309601 | SNP | T | A | 61 | 77 | | 79.2% | 81.6% | 80.4% |
| Pillar | 4309605 | SNP | G | T | 60 | 75 | | 80.0% | 83.3% | 81.7% |
| Pillar | 4320813 | SNP | A | G | 33 | 42 | | 78.6% | 80.6% | 79.6% |
| Pillar | 4323834 | SNP | C | A | 30 | 40 | | 75.0% | 82.6% | 78.8% |
| Pillar | 4323836 | SNP | G | T | 30 | 40 | | 75.0% | 82.6% | 78.8% |
| Pillar | 4324716 | SNP | T | C | 26 | 31 | | 83.9% | 76.9% | 80.4% |
| Pillar | 4328281 | SNP | T | C | 67 | 89 | | 75.3% | 75.4% | 75.4% |
| Pillar | 4342913 | SNP | T | G | 46 | 57 | | 80.7% | 78.1% | 79.4% |
| Pillar | 4342928 | SNP | T | C | 45 | 56 | | 80.4% | 80.8% | 80.6% |
| Pillar | 4350691 | SNP | G | A | 30 | 40 | | 75.0% | 80.0% | 77.5% |
| Pillar | 4352413 | SNP | G | A | 42 | 53 | | 79.2% | 79.4% | 79.3% |
| Pillar | 4361117 | DIP | — | A | 20 | 24 | | 83.3% | 87.5% | 85.4% |
| Pillar | 4365985 | SNP | C | T | 81 | 106 | | 76.4% | 78.3% | 77.4% |
| Pillar | 4375514 | DIP | A | — | 14 | 17 | | 82.4% | 88.0% | 85.2% |
| Pillar | 4376149 | SNP | T | C | 23 | 29 | | 79.3% | 85.7% | 82.5% |
| Pillar | 4387505 | SNP | A | G | 49 | 65 | | 75.4% | 79.5% | 77.5% |
| Pillar | 4387989 | SNP | C | T | 38 | 45 | | 84.4% | 77.5% | 81.0% |
| Pillar | 4406688 | SNP | C | G | 23 | 27 | | 85.2% | 78.1% | 81.7% |
| Pillar | 4406989 | SNP | T | C | 45 | 57 | | 78.9% | 80.4% | 79.7% |
| Pillar | 4407585 | SNP | A | C | 59 | 76 | | 77.6% | 80.0% | 78.8% |
| Pillar | 4408423 | SNP | T | C | 39 | 51 | | 76.5% | 75.0% | 75.8% |
| Pillar | 4408702 | SNP | C | T | 57 | 73 | | 78.1% | 77.1% | 77.6% |
| Pillar | 4419444 | SNP | C | T | 34 | 44 | | 77.3% | 75.9% | 76.6% |
| Pillar | 4460070 | SNP | T | C | 27 | 36 | | 75.0% | 75.6% | 75.3% |
| Pillar | 4567254 | SNP | A | C | 69 | 90 | Glu520Ala | 76.7% | 76.2% | 76.5% |
| Pillar | 4643478 | SNP | A | G | 78 | 101 | | 77.2% | 76.3% | 76.8% |
| Pillar | 4714899 | SNP | T | C | 46 | 61 | | 75.4% | 76.5% | 76.0% |
| Pillar | 4735286 | SNP | T | C | 36 | 43 | | 83.7% | 81.8% | 82.8% |
| Pillar | 4735288 | SNP | A | C | 36 | 43 | | 83.7% | 81.4% | 82.6% |
| Pillar | 4737120 | SNP | G | C | 43 | 57 | 3'-utr | 75.4% | 76.6% | 76.0% |
| Pillar | 4778682 | SNP | T | A | 52 | 67 | | 77.6% | 75.9% | 76.8% |
| Pillar | 4810496 | SNP | G | A | 31 | 40 | | 77.5% | 77.4% | 77.5% |
| Pillar | 4810515 | SNP | T | C | 40 | 51 | | 78.4% | 76.7% | 77.6% |
| Pillar | 4810823 | SNP | G | A | 40 | 52 | | 76.9% | 86.7% | 81.8% |
| Pillar | 4810959 | SNP | A | G | 44 | 56 | | 78.6% | 76.5% | 77.6% |
| Pillar | 4829143 | SNP | C | G | 39 | 52 | | 75.0% | 75.0% | 75.0% |
| Pillar | 4829554 | SNP | G | A | 73 | 95 | | 76.8% | 76.5% | 76.7% |
| Pillar | 4836416 | SNP | A | G | 43 | 54 | | 79.6% | 76.9% | 78.3% |
| Pillar | 4888116 | SNP | T | G | 71 | 94 | | 75.5% | 75.4% | 75.5% |
| Pillar | 4952127 | SNP | C | A | 54 | 70 | 3'-utr | 77.1% | 77.1% | 77.1% |
| Pillar | 4955055 | SNP | A | C | 45 | 59 | | 76.3% | 80.4% | 78.4% |
| Pillar | 4955073 | SNP | A | C | 47 | 58 | | 81.0% | 83.7% | 82.4% |
| Pillar | 4955346 | SNP | C | G | 52 | 60 | | 86.7% | 80.0% | 83.4% |
| Pillar | 4967532 | SNP | G | A | 32 | 40 | | 80.0% | 81.5% | 80.8% |
| Pillar | 4967534 | SNP | G | A | 30 | 38 | | 78.9% | 81.5% | 80.2% |
| Pillar | 4967550 | SNP | G | A | 31 | 37 | | 83.8% | 77.8% | 80.8% |
| Pillar | 4974736 | SNP | T | C | 48 | 60 | | 80.0% | 80.0% | 80.0% |
| Pillar | 4974745 | SNP | C | T | 49 | 62 | | 79.0% | 78.7% | 78.9% |
| Pillar | 4974783 | SNP | A | G | 45 | 60 | | 75.0% | 78.0% | 76.5% |
| Pillar | 4975976 | SNP | A | G | 43 | 57 | | 75.4% | 75.0% | 75.2% |
| Pillar | 5009955 | SNP | C | T | 55 | 70 | | 78.6% | 76.2% | 77.4% |
| Pillar | 5010011 | SNP | A | C | 52 | 63 | | 82.5% | 80.4% | 81.5% |
| Pillar | 5010203 | SNP | G | T | 56 | 74 | | 75.7% | 79.1% | 77.4% |
| Pillar | 5010491 | SNP | A | T | 50 | 66 | | 75.8% | 82.8% | 79.3% |
| Pillar | 5010504 | SNP | T | C | 57 | 74 | | 77.0% | 79.6% | 78.3% |
| Pillar | 5010521 | SNP | C | T | 57 | 74 | | 77.0% | 77.6% | 77.3% |
| Pillar | 5013825 | SNP | T | C | 48 | 62 | | 77.4% | 75.6% | 76.5% |
| Pillar | 5018112 | SNP | C | A | 64 | 81 | | 79.0% | 76.1% | 77.6% |
| Pillar | 5020476 | SNP | G | T | 40 | 53 | | 75.5% | 75.0% | 75.3% |
| Pillar | 5023425 | SNP | G | A | 38 | 49 | | 77.6% | 78.0% | 77.8% |
| Pillar | 5029625 | SNP | A | C | 61 | 79 | | 77.2% | 77.4% | 77.3% |
| Pillar | 5049191 | SNP | T | C | 58 | 75 | | 77.3% | 76.7% | 77.0% |
| Pillar | 5053437 | SNP | T | C | 50 | 63 | | 79.4% | 75.5% | 77.5% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Pillar | 5053651 | SNP | C | T | 49 | 61 | | 80.3% | 80.8% | 80.6% |
| Pillar | 5060398 | SNP | A | G | 44 | 56 | | 78.6% | 78.3% | 78.5% |
| Pillar | 5060399 | SNP | T | C | 44 | 57 | | 77.2% | 78.3% | 77.8% |
| Pillar | 5071880 | SNP | T | C | 27 | 35 | | 77.1% | 84.0% | 80.6% |
| Pillar | 5072548 | SNP | G | A | 31 | 41 | | 75.6% | 78.7% | 77.2% |
| Pillar | 5079008 | SNP | G | T | 56 | 74 | 3'-utr | 75.7% | 77.9% | 76.8% |
| Pillar | 5080421 | SNP | T | C | 29 | 38 | | 76.3% | 75.0% | 75.7% |
| Pillar | 5080430 | SNP | A | G | 28 | 37 | | 75.7% | 80.8% | 78.3% |
| Pillar | 5349691 | SNP | G | C | 42 | 56 | | 75.0% | 75.0% | 75.0% |
| Pillar | 5351512 | SNP | G | A | 25 | 32 | | 78.1% | 77.8% | 78.0% |
| Pillar | 5352812 | SNP | C | T | 51 | 64 | | 79.7% | 75.4% | 77.6% |
| Pillar | 5366886 | SNP | C | T | 40 | 51 | | 78.4% | 77.3% | 77.9% |
| Pillar | 5367133 | SNP | C | T | 49 | 64 | | 76.6% | 76.9% | 76.8% |
| Pillar | 5367136 | SNP | C | T | 49 | 65 | | 75.4% | 78.6% | 77.0% |
| Pillar | 5368156 | SNP | G | A | 51 | 68 | | 75.0% | 75.8% | 75.4% |
| Pillar | 5464390 | SNP | T | C | 38 | 50 | | 76.0% | 77.1% | 76.6% |
| Pillar | 5472285 | SNP | T | A | 56 | 72 | Asn422Lys | 77.8% | 80.0% | 78.9% |
| Pillar | 5472324 | SNP | A | T | 48 | 62 | Arg435Ser | 77.4% | 77.5% | 77.5% |
| Pillar | 5477814 | SNP | G | A | 35 | 45 | | 77.8% | 76.7% | 77.3% |
| Pillar | 5478079 | SNP | C | T | 30 | 35 | | 85.7% | 84.0% | 84.9% |
| Pillar | 5478346 | DIP | — | C | 18 | 24 | | 75.0% | 79.8% | 77.4% |
| Pillar | 5478365 | SNP | T | C | 29 | 38 | | 76.3% | 78.1% | 77.2% |
| Pillar | 5478368 | SNP | T | C | 28 | 37 | | 75.7% | 78.1% | 76.9% |
| Pillar | 5480979 | SNP | C | A | 55 | 72 | | 76.4% | 83.3% | 79.9% |
| Pillar | 5481013 | SNP | T | C | 36 | 48 | | 75.0% | 80.0% | 77.5% |
| Pillar | 5481014 | SNP | C | T | 36 | 48 | | 75.0% | 80.0% | 77.5% |
| Pillar | 5492877 | SNP | T | A | 36 | 45 | | 80.0% | 86.5% | 83.3% |
| Pillar | 5492884 | SNP | T | A | 37 | 47 | | 78.7% | 88.2% | 83.5% |
| Pillar | 5493003 | SNP | C | A | 21 | 28 | | 75.0% | 76.5% | 75.8% |
| Pillar | 5574833 | SNP | T | C | 39 | 52 | | 75.0% | 82.6% | 78.8% |
| Pillar | 5575762 | SNP | T | C | 24 | 32 | | 75.0% | 75.0% | 75.0% |
| Pillar | 5575766 | SNP | C | T | 22 | 29 | | 75.9% | 75.0% | 75.5% |
| Pillar | 5578396 | SNP | A | C | 33 | 41 | | 80.5% | 80.0% | 80.3% |
| Pillar | 5582440 | SNP | T | A | 41 | 54 | | 75.9% | 76.9% | 76.4% |
| Pillar | 5582441 | SNP | T | A | 42 | 56 | | 75.0% | 76.9% | 76.0% |
| Pillar | 5582444 | SNP | T | A | 42 | 56 | | 75.0% | 76.5% | 75.8% |
| Pillar | 5713887 | SNP | C | T | 27 | 33 | | 81.8% | 85.2% | 83.5% |
| Pillar | 5715276 | SNP | C | A | 53 | 67 | 3'-utr | 79.1% | 75.4% | 77.3% |
| Pillar | 5719628 | SNP | A | G | 25 | 33 | | 75.8% | 78.3% | 77.1% |
| Pillar | 5725846 | SNP | C | T | 52 | 64 | | 81.2% | 75.0% | 78.1% |
| Pillar | 5725850 | SNP | A | C | 48 | 60 | | 80.0% | 75.0% | 77.5% |
| Pillar | 5742143 | SNP | C | G | 22 | 29 | | 75.9% | 83.3% | 79.6% |
| Pillar | 5772924 | SNP | C | T | 54 | 71 | | 76.1% | 79.7% | 77.9% |
| Pillar | 5799474 | SNP | A | G | 94 | 116 | | 81.0% | 80.0% | 80.5% |
| Pillar | 5838993 | SNP | G | A | 50 | 66 | | 75.8% | 77.3% | 76.6% |
| Pillar | 5841662 | SNP | A | G | 27 | 36 | | 75.0% | 79.4% | 77.2% |
| Pillar | 5856854 | SNP | C | T | 30 | 37 | | 81.1% | 75.0% | 78.1% |
| Pillar | 5864354 | SNP | G | A | 41 | 52 | | 78.8% | 78.8% | 78.8% |
| Pillar | 5866247 | SNP | T | G | 30 | 40 | | 75.0% | 78.3% | 76.7% |
| Standard | 10697920 | SNP | T | G | 41 | 49 | | 83.7% | 77.1% | 80.4% |
| Standard | 10752012 | SNP | A | G | 24 | 31 | | 77.4% | 80.4% | 78.9% |
| Standard | 10760274 | SNP | C | G | 45 | 58 | | 77.6% | 79.3% | 78.5% |
| Standard | 10781158 | SNP | C | T | 29 | 38 | | 76.3% | 77.0% | 76.7% |
| Standard | 10782284 | SNP | G | A | 45 | 59 | | 76.3% | 80.6% | 78.5% |
| Standard | 10782290 | SNP | T | C | 42 | 54 | | 77.8% | 77.9% | 77.9% |
| Standard | 10782293 | SNP | T | C | 43 | 55 | | 78.2% | 78.6% | 78.4% |
| Standard | 10784536 | SNP | T | C | 42 | 56 | | 75.0% | 77.1% | 76.1% |
| Standard | 10801148 | SNP | G | A | 45 | 58 | | 77.6% | 76.9% | 77.3% |
| Standard | 10801173 | SNP | C | T | 40 | 53 | | 75.5% | 75.0% | 75.3% |
| Standard | 10801755 | SNP | G | C | 26 | 32 | | 81.2% | 80.8% | 81.0% |
| Standard | 10801760 | SNP | T | C | 26 | 33 | | 78.8% | 79.6% | 79.2% |
| Standard | 10801769 | SNP | C | T | 27 | 35 | | 77.1% | 78.8% | 78.0% |
| Standard | 10817289 | SNP | A | G | 46 | 61 | Asn197Asp | 75.4% | 80.0% | 77.7% |
| Standard | 10817542 | SNP | G | C | 44 | 52 | | 84.6% | 81.0% | 82.8% |
| Standard | 10817555 | SNP | G | A | 41 | 51 | | 80.4% | 80.5% | 80.5% |
| Standard | 10817567 | SNP | A | T | 42 | 55 | | 76.4% | 76.3% | 76.4% |
| Standard | 10817712 | SNP | C | T | 24 | 32 | | 75.0% | 82.9% | 79.0% |
| Standard | 10819518 | SNP | T | C | 28 | 35 | | 80.0% | 92.7% | 86.4% |
| Standard | 10819939 | SNP | T | C | 24 | 31 | | 77.4% | 76.6% | 77.0% |
| Standard | 10820222 | SNP | T | G | 34 | 38 | | 89.5% | 79.1% | 84.3% |
| Standard | 10820965 | SNP | C | G | 22 | 28 | | 78.6% | 81.4% | 80.0% |
| Standard | 10821193 | SNP | A | G | 35 | 45 | | 77.8% | 75.3% | 76.6% |
| Standard | 10821253 | SNP | G | A | 29 | 35 | | 82.9% | 78.9% | 80.9% |
| Standard | 10821259 | SNP | C | T | 29 | 36 | | 80.6% | 79.2% | 79.9% |
| Standard | 10821267 | SNP | G | A | 30 | 38 | | 78.9% | 76.8% | 77.9% |
| Standard | 10821482 | SNP | G | A | 30 | 39 | | 76.9% | 87.0% | 82.0% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Standard | 10821502 | SNP | G | A | 37 | 49 | | 75.5% | 89.8% | 82.7% |
| Standard | 10846491 | SNP | C | T | 29 | 38 | | 76.3% | 77.6% | 77.0% |
| Standard | 10858554 | SNP | A | C | 24 | 30 | | 80.0% | 77.2% | 78.6% |
| Standard | 10858564 | SNP | A | G | 21 | 27 | | 77.8% | 77.8% | 77.8% |
| Standard | 10858821 | SNP | C | A | 30 | 38 | | 78.9% | 77.0% | 78.0% |
| Standard | 10858877 | SNP | G | T | 27 | 36 | | 75.0% | 78.8% | 76.9% |
| Standard | 10860892 | SNP | T | C | 27 | 35 | | 77.1% | 81.6% | 79.4% |
| Standard | 10862276 | SNP | C | T | 36 | 47 | | 76.6% | 77.9% | 77.3% |
| Standard | 10864940 | SNP | G | A | 32 | 39 | | 82.1% | 80.6% | 81.4% |
| Standard | 10865397 | SNP | G | T | 28 | 34 | | 82.4% | 75.6% | 79.0% |
| Standard | 10867613 | SNP | C | T | 38 | 50 | Ser27Leu | 76.0% | 79.3% | 77.7% |
| Standard | 10868435 | SNP | T | C | 33 | 43 | | 76.7% | 77.8% | 77.3% |
| Standard | 10868723 | SNP | A | G | 31 | 39 | | 79.5% | 82.4% | 81.0% |
| Standard | 10868757 | SNP | C | A | 24 | 32 | | 75.0% | 86.7% | 80.9% |
| Standard | 10868758 | SNP | A | G | 24 | 32 | | 75.0% | 86.7% | 80.9% |
| Standard | 10868970 | SNP | G | A | 28 | 37 | | 75.7% | 92.1% | 83.9% |
| Standard | 10868993 | SNP | C | T | 33 | 43 | | 76.7% | 96.7% | 86.7% |
| Standard | 10869245 | SNP | T | A | 34 | 44 | | 77.3% | 89.1% | 83.2% |
| Standard | 10869292 | SNP | G | T | 34 | 43 | | 79.1% | 83.3% | 81.2% |
| Standard | 10869552 | DIP | T | — | 22 | 29 | | 75.9% | 84.2% | 80.1% |
| Standard | 10869559 | SNP | T | A | 23 | 30 | | 76.7% | 86.4% | 81.6% |
| Standard | 10869823 | SNP | A | G | 31 | 40 | | 77.5% | 75.0% | 76.3% |
| Standard | 10869825 | SNP | T | C | 31 | 40 | | 77.5% | 76.7% | 77.1% |
| Standard | 10869830 | SNP | G | T | 29 | 37 | | 78.4% | 80.6% | 79.5% |
| Standard | 10869842 | SNP | A | G | 25 | 33 | | 75.8% | 86.2% | 81.0% |
| Standard | 10884573 | SNP | T | A | 22 | 29 | | 75.9% | 91.9% | 83.9% |
| Standard | 10884580 | SNP | C | T | 22 | 29 | | 75.9% | 97.1% | 86.5% |
| Standard | 10884785 | SNP | A | G | 29 | 37 | | 78.4% | 90.3% | 84.4% |
| Standard | 10884940 | SNP | T | C | 32 | 40 | | 80.0% | 78.9% | 79.5% |
| Standard | 10885036 | SNP | A | G | 27 | 34 | | 79.4% | 76.6% | 78.0% |
| Standard | 10885189 | SNP | T | C | 31 | 41 | | 75.6% | 82.3% | 79.0% |
| Standard | 10885263 | SNP | C | A | 28 | 37 | | 75.7% | 78.1% | 76.9% |
| Standard | 10887550 | SNP | T | A | 33 | 44 | | 75.0% | 86.4% | 80.7% |
| Standard | 10889375 | SNP | G | A | 42 | 56 | | 75.0% | 87.7% | 81.4% |
| Standard | 10889415 | SNP | T | G | 41 | 52 | | 78.8% | 79.7% | 79.3% |
| Standard | 10890984 | SNP | G | A | 26 | 34 | | 76.5% | 75.0% | 75.8% |
| Standard | 10891010 | SNP | T | C | 30 | 38 | | 78.9% | 80.6% | 79.8% |
| Standard | 10891015 | SNP | C | T | 27 | 36 | | 75.0% | 80.6% | 77.8% |
| Standard | 10892142 | SNP | T | C | 34 | 44 | | 77.3% | 83.0% | 80.2% |
| Standard | 10892264 | SNP | C | T | 21 | 26 | | 80.8% | 78.3% | 79.6% |
| Standard | 10892844 | SNP | T | C | 43 | 51 | | 84.3% | 84.8% | 84.6% |
| Standard | 10893179 | SNP | A | G | 44 | 49 | | 89.8% | 81.2% | 85.5% |
| Standard | 10893310 | SNP | A | C | 32 | 41 | | 78.0% | 80.7% | 79.4% |
| Standard | 10893696 | SNP | C | T | 59 | 74 | Val432Ile | 79.7% | 77.0% | 78.4% |
| Standard | 10893943 | SNP | C | G | 62 | 81 | | 76.5% | 76.0% | 76.3% |
| Standard | 10894900 | SNP | G | T | 53 | 69 | | 76.8% | 78.9% | 77.9% |
| Pillar | 11945528 | SNP | C | T | 62 | 82 | | 75.6% | 77.1% | 76.4% |
| Standard | 12666240 | SNP | C | A | 34 | 45 | | 75.6% | 87.9% | 81.8% |
| Pillar | 12776159 | SNP | G | A | 30 | 35 | | 85.7% | 76.5% | 81.1% |
| Pillar | 13141873 | SNP | G | T | 51 | 60 | | 85.0% | 81.8% | 83.4% |
| Pillar | 13367722 | SNP | G | T | 101 | 126 | | 80.2% | #VALUE! | 80.2% |
| Pillar | 13367727 | SNP | A | C | 101 | 132 | | 76.5% | 84.0% | 80.3% |
| Pillar | 13763233 | SNP | A | C | 58 | 72 | | 80.6% | 79.5% | 80.1% |
| Pillar | 13772198 | SNP | G | A | 64 | 82 | | 78.0% | 83.3% | 80.7% |
| Pillar | 13780242 | SNP | T | C | 44 | 53 | | 83.0% | 77.6% | 80.3% |
| Pillar | 13796412 | SNP | A | C | 29 | 37 | | 78.4% | 75.0% | 76.7% |
| Pillar | 13797328 | SNP | T | A | 26 | 32 | | 81.2% | 86.4% | 83.8% |
| Pillar | 13815018 | SNP | A | T | 41 | 51 | | 80.4% | 75.0% | 77.7% |
| Pillar | 13815439 | SNP | T | C | 44 | 56 | | 78.6% | 77.6% | 78.1% |
| Pillar | 13817350 | SNP | T | C | 46 | 54 | | 85.2% | 77.8% | 81.5% |
| Pillar | 13828168 | SNP | G | A | 40 | 49 | | 81.6% | 80.0% | 80.8% |
| Pillar | 13831534 | SNP | G | A | 61 | 77 | | 79.2% | 75.4% | 77.3% |
| Pillar | 13840465 | SNP | G | T | 54 | 66 | | 81.8% | 86.2% | 84.0% |
| Pillar | 13858848 | SNP | C | G | 61 | 69 | | 88.4% | 78.6% | 83.5% |
| Pillar | 13863936 | SNP | A | G | 37 | 46 | | 80.4% | 76.2% | 78.3% |
| Pillar | 13864027 | SNP | G | A | 33 | 41 | | 80.5% | 76.9% | 78.7% |
| Pillar | 13865644 | SNP | T | A | 38 | 46 | | 82.6% | 80.8% | 81.7% |
| Pillar | 13866046 | SNP | G | T | 44 | 55 | | 80.0% | 96.8% | 88.4% |
| Pillar | 13876718 | SNP | C | A | 35 | 46 | | 76.1% | 81.1% | 78.6% |
| Pillar | 13876933 | SNP | G | A | 44 | 53 | | 83.0% | 84.7% | 83.9% |
| Pillar | 13877901 | SNP | C | T | 52 | 69 | | 75.4% | 78.9% | 77.2% |
| Pillar | 13877918 | SNP | G | A | 54 | 72 | | 75.0% | 79.3% | 77.2% |
| Pillar | 13878338 | SNP | T | C | 67 | 73 | | 91.8% | 77.1% | 84.5% |
| Pillar | 13881346 | SNP | T | C | 53 | 61 | | 86.9% | 76.2% | 81.6% |
| Pillar | 13885101 | SNP | A | T | 24 | 28 | | 85.7% | 90.0% | 87.9% |
| Pillar | 13896416 | SNP | G | T | 92 | 105 | | 87.6% | 75.9% | 81.8% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Pillar | 13905434 | SNP | T | C | 73 | 92 | | 79.3% | 77.8% | 78.6% |
| Pillar | 13909285 | SNP | A | G | 80 | 100 | | 80.0% | 75.0% | 77.5% |
| Pillar | 13931290 | SNP | G | A | 35 | 45 | | 77.8% | 75.9% | 76.9% |
| Pillar | 13931393 | SNP | A | C | 40 | 49 | | 81.6% | 78.8% | 80.2% |
| Pillar | 13932693 | SNP | G | A | 50 | 60 | | 83.3% | 78.0% | 80.7% |
| Pillar | 13933926 | SNP | C | T | 42 | 56 | | 75.0% | 75.9% | 75.5% |
| Pillar | 13938194 | SNP | T | C | 59 | 71 | | 83.1% | 81.0% | 82.1% |
| Pillar | 13940390 | SNP | G | A | 36 | 40 | | 90.0% | 80.0% | 85.0% |
| Pillar | 13946846 | SNP | C | T | 54 | 70 | | 77.1% | 82.6% | 79.9% |
| Pillar | 13950208 | SNP | G | A | 43 | 57 | | 75.4% | 75.0% | 75.2% |
| Pillar | 13951963 | SNP | C | T | 61 | 77 | | 79.2% | 75.0% | 77.1% |
| Pillar | 13952146 | SNP | A | C | 52 | 67 | | 77.6% | 86.0% | 81.8% |
| Pillar | 13954096 | SNP | G | A | 48 | 55 | | 87.3% | 80.4% | 83.9% |
| Pillar | 13957732 | DIP | — | T | 35 | 44 | | 79.5% | 77.1% | 78.3% |
| Pillar | 13959436 | SNP | G | T | 62 | 78 | | 79.5% | 83.0% | 81.3% |
| Pillar | 13959574 | SNP | C | G | 55 | 68 | | 80.9% | 84.8% | 82.9% |
| Pillar | 13959774 | SNP | A | G | 53 | 63 | | 84.1% | 78.3% | 81.2% |
| Pillar | 13959796 | SNP | T | C | 52 | 68 | | 76.5% | 80.0% | 78.3% |
| Pillar | 13959879 | SNP | T | C | 49 | 60 | | 81.7% | 79.2% | 80.5% |
| Pillar | 13963479 | SNP | A | G | 28 | 37 | | 75.7% | 80.0% | 77.9% |
| Pillar | 13963872 | SNP | C | T | 34 | 42 | | 81.0% | 78.9% | 80.0% |
| Pillar | 13965454 | SNP | G | T | 45 | 60 | | 75.0% | 88.9% | 82.0% |
| Pillar | 13965465 | SNP | A | G | 48 | 64 | | 75.0% | 91.1% | 83.1% |
| Pillar | 13965632 | SNP | C | G | 73 | 87 | | 83.9% | 81.0% | 82.5% |
| Pillar | 13980604 | DIP | T | — | 32 | 39 | | 82.1% | 99.2% | 90.7% |
| Pillar | 13980822 | SNP | G | A | 37 | 44 | | 84.1% | 82.9% | 83.5% |
| Pillar | 13980826 | SNP | C | T | 37 | 44 | | 84.1% | 82.9% | 83.5% |
| Pillar | 13980844 | SNP | T | A | 35 | 40 | | 87.5% | 78.9% | 83.2% |
| Pillar | 13980904 | SNP | A | G | 35 | 39 | | 89.7% | 84.2% | 87.0% |
| Pillar | 13980921 | SNP | A | G | 42 | 45 | | 93.3% | 78.9% | 86.1% |
| Pillar | 13981111 | SNP | A | C | 45 | 51 | | 88.2% | 79.2% | 83.7% |
| Pillar | 13981146 | SNP | C | T | 47 | 55 | | 85.5% | 79.2% | 82.4% |
| Pillar | 13981153 | SNP | G | A | 48 | 57 | | 84.2% | 81.8% | 83.0% |
| Pillar | 13981165 | SNP | C | A | 45 | 55 | | 81.8% | 84.0% | 82.9% |
| Pillar | 13982544 | SNP | T | G | 37 | 48 | | 77.1% | 80.0% | 78.6% |
| Pillar | 13982901 | SNP | A | G | 54 | 63 | | 85.7% | 83.3% | 84.5% |
| Pillar | 13982948 | SNP | T | C | 42 | 52 | | 80.8% | 89.7% | 85.3% |
| Pillar | 13983019 | SNP | A | G | 33 | 44 | | 75.0% | 83.9% | 79.5% |
| Pillar | 13983036 | SNP | G | A | 35 | 46 | | 76.1% | 83.8% | 80.0% |
| Pillar | 13983155 | SNP | C | A | 36 | 44 | | 81.8% | 80.0% | 80.9% |
| Pillar | 13983285 | DIP | TT | — | 17 | 22 | | 77.3% | 76.2% | 76.8% |
| Pillar | 13983567 | SNP | T | A | 38 | 45 | | 84.4% | 78.1% | 81.3% |
| Pillar | 13984153 | SNP | T | C | 37 | 48 | | 77.1% | 80.4% | 78.8% |
| Pillar | 13984593 | SNP | A | G | 71 | 89 | | 79.8% | 78.1% | 79.0% |
| Pillar | 13984620 | SNP | G | A | 68 | 89 | | 76.4% | 80.3% | 78.4% |
| Pillar | 13984665 | SNP | A | C | 82 | 99 | | 82.8% | 84.1% | 83.5% |
| Pillar | 13984666 | SNP | G | A | 81 | 98 | | 82.7% | 85.2% | 84.0% |
| Pillar | 13985885 | SNP | C | T | 57 | 65 | | 87.7% | 78.4% | 83.1% |
| Pillar | 13986150 | SNP | C | A | 58 | 69 | | 84.1% | 86.0% | 85.1% |
| Pillar | 13986225 | SNP | A | G | 55 | 69 | | 79.7% | 84.9% | 82.3% |
| Pillar | 13986239 | SNP | C | G | 50 | 65 | | 76.9% | 80.3% | 78.6% |
| Pillar | 13986268 | SNP | C | T | 45 | 57 | | 78.9% | 79.4% | 79.2% |
| Pillar | 13986279 | SNP | A | G | 36 | 46 | | 78.3% | 81.0% | 79.7% |
| Pillar | 13986287 | SNP | C | T | 33 | 41 | | 80.5% | 76.3% | 78.4% |
| Pillar | 13986423 | SNP | A | G | 58 | 74 | | 78.4% | 84.4% | 81.4% |
| Pillar | 13986799 | SNP | T | A | 32 | 42 | | 76.2% | 84.0% | 80.1% |
| Pillar | 13986816 | SNP | A | C | 38 | 49 | | 77.6% | 86.5% | 82.1% |
| Pillar | 13987542 | SNP | G | A | 69 | 81 | | 85.2% | 83.6% | 84.4% |
| Pillar | 13987547 | SNP | T | C | 75 | 87 | | 86.2% | 83.3% | 84.8% |
| Pillar | 13987569 | SNP | G | A | 69 | 81 | | 85.2% | 79.7% | 82.5% |
| Pillar | 13987645 | SNP | A | G | 76 | 88 | | 86.4% | 76.0% | 81.2% |
| Pillar | 13988031 | SNP | A | G | 26 | 32 | | 81.2% | 75.0% | 78.1% |
| Pillar | 13988035 | SNP | C | T | 26 | 32 | | 81.2% | 75.0% | 78.1% |
| Pillar | 13988192 | SNP | G | A | 60 | 78 | | 76.9% | 77.6% | 77.3% |
| Pillar | 13988253 | SNP | T | C | 63 | 79 | | 79.7% | 77.5% | 78.6% |
| Pillar | 13988419 | SNP | G | T | 108 | 133 | | 81.2% | 76.0% | 78.6% |
| Pillar | 13988454 | SNP | C | T | 108 | 133 | | 81.2% | 78.4% | 79.8% |
| Pillar | 13988673 | SNP | T | C | 91 | 114 | | 79.8% | 75.6% | 77.7% |
| Pillar | 13988737 | SNP | G | A | 93 | 114 | | 81.6% | 76.8% | 79.2% |
| Pillar | 13988877 | SNP | T | C | 64 | 84 | | 76.2% | 75.8% | 76.0% |
| Pillar | 13988982 | SNP | A | G | 52 | 69 | | 75.4% | 75.7% | 75.6% |
| Pillar | 13988989 | SNP | A | G | 55 | 70 | | 78.6% | 76.4% | 77.5% |
| Pillar | 13989034 | SNP | G | A | 53 | 61 | | 86.9% | 81.2% | 84.1% |
| Pillar | 13989037 | SNP | T | G | 52 | 60 | | 86.7% | 80.6% | 83.7% |
| Pillar | 13989907 | SNP | A | C | 63 | 74 | Ile53Leu | 85.1% | 78.3% | 81.7% |
| Pillar | 13990669 | SNP | G | A | 44 | 55 | | 80.0% | 77.6% | 78.8% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Pillar | 13994305 | SNP | G | A | 51 | 56 | | 91.1% | 76.2% | 83.7% |
| Pillar | 14889259 | SNP | G | A | 48 | 59 | | 81.4% | 75.0% | 78.2% |
| Standard | 15395921 | SNP | G | A | 50 | 61 | | 82.0% | 85.1% | 83.6% |
| Standard | 16226400 | SNP | T | C | 53 | 65 | | 81.5% | 91.8% | 86.7% |
| Standard* | 17054070 | Insertion | — | TCTCTCTCTCTCTCTCTC | 28 | 32 | Intron | 87.5% | 95.7% | 91.6% |
| Standard | 17143457 | SNP | C | T | 24 | 28 | | 85.7% | 87.5% | 86.6% |
| Standard | 17454131 | DIP | GT | — | 24 | 29 | | 82.8% | | 82.8% |
| Standard | 17456673 | SNP | T | C | 38 | 41 | | 92.7% | 90.2% | 91.5% |
| Standard | 17456688 | SNP | T | C | 32 | 37 | | 86.5% | 90.6% | 88.6% |
| Standard | 17456690 | SNP | C | T | 33 | 38 | | 86.8% | 90.6% | 88.7% |
| Standard | 17456693 | SNP | C | T | 34 | 39 | | 87.2% | 90.6% | 88.9% |
| Standard | 17456708 | DIP | T | — | 32 | 39 | | 82.1% | 90.6% | 86.4% |
| Standard | 17456710 | SNP | T | A | 27 | 34 | | 79.4% | 90.6% | 85.0% |
| Standard | 17456713 | SNP | T | A | 28 | 34 | | 82.4% | 90.6% | 86.5% |
| Standard | 17457834 | SNP | C | T | 53 | 64 | | 82.8% | 94.0% | 88.4% |
| Standard | 17458415 | SNP | A | G | 38 | 41 | | 92.7% | 89.6% | 91.2% |
| Standard | 17459129 | SNP | C | T | 46 | 50 | | 92.0% | 95.0% | 93.5% |
| Standard | 17460475 | SNP | G | A | 36 | 44 | | 81.8% | 97.0% | 89.4% |
| Standard | 17460658 | SNP | A | G | 30 | 35 | | 85.7% | 92.5% | 89.1% |
| Standard | 17460735 | SNP | A | G | 37 | 41 | | 90.2% | 93.0% | 91.6% |
| Standard | 17460919 | DIP | — | A | 34 | 38 | | 89.5% | 87.9% | 88.7% |
| Standard | 17460958 | SNP | T | C | 31 | 36 | | 86.1% | 87.3% | 86.7% |
| Standard | 17460986 | DIP | TG | — | 28 | 33 | | 84.8% | 91.4% | 88.1% |
| Standard | 17460993 | SNP | A | G | 35 | 39 | | 89.7% | 89.1% | 89.4% |
| Standard | 17461015 | SNP | C | G | 29 | 33 | | 87.9% | 86.0% | 87.0% |
| Standard | 17461028 | SNP | A | C | 31 | 35 | | 88.6% | 85.4% | 87.0% |
| Standard | 17461031 | DIP | A | — | 29 | 34 | | 85.3% | 85.4% | 85.4% |
| Standard | 17461083 | DIP | — | A | 33 | 38 | | 86.8% | 91.8% | 89.3% |
| Standard | 17461112 | SNP | A | T | 35 | 39 | | 89.7% | 96.7% | 93.2% |
| Standard | 17461116 | SNP | A | G | 33 | 37 | | 89.2% | 96.8% | 93.0% |
| Standard* | 17461131 | Insertion | N/A | undefined element | 57 | 63 | | 90.5% | 86.6% | 88.6% |
| Standard | 17461132 | SNP | C | A | 26 | 32 | | 81.2% | 96.8% | 89.0% |
| Standard | 17461209 | SNP | T | C | 21 | 26 | | 80.8% | 88.7% | 84.8% |
| Standard | 17461210 | SNP | T | C | 21 | 26 | | 80.8% | 88.7% | 84.8% |
| Standard | 17461534 | SNP | C | T | 38 | 42 | | 90.5% | 96.6% | 93.6% |
| Standard | 17461569 | SNP | C | T | 41 | 47 | | 87.2% | 88.3% | 87.8% |
| Standard | 17461584 | SNP | A | G | 41 | 47 | | 87.2% | 88.7% | 88.0% |
| Standard | 17461745 | SNP | A | T | 25 | 27 | | 92.6% | 82.9% | 87.8% |
| Standard | 17462032 | DIP | — | C | 38 | 45 | | 84.4% | 89.8% | 87.1% |
| Standard | 17462161 | SNP | T | A | 53 | 66 | | 80.3% | 96.1% | 88.2% |
| Standard | 17462280 | SNP | G | T | 29 | 33 | | 87.9% | 91.7% | 89.8% |
| Standard | 17462765 | SNP | G | A | 32 | 36 | | 88.9% | 88.7% | 88.8% |
| Standard | 17463148 | DIP | — | A | 28 | 32 | | 87.5% | 93.0% | 90.3% |
| Standard | 17463324 | SNP | T | G | 32 | 37 | | 86.5% | 92.3% | 89.4% |
| Standard | 17463896 | SNP | T | C | 55 | 66 | | 83.3% | 92.9% | 88.1% |
| Standard | 17464158 | SNP | T | C | 44 | 52 | | 84.6% | 91.7% | 88.2% |
| Standard | 17464542 | SNP | C | A | 49 | 51 | | 96.1% | 91.0% | 93.6% |
| Standard | 17464778 | SNP | A | T | 29 | 37 | | 78.4% | 88.9% | 83.7% |
| Standard | 17464873 | SNP | T | C | 43 | 49 | | 87.8% | 94.2% | 91.0% |
| Standard | 17465014 | SNP | C | T | 41 | 51 | | 80.4% | 90.4% | 85.4% |
| Standard | 17465595 | SNP | A | G | 51 | 56 | | 91.1% | 93.7% | 92.4% |
| Standard | 17467679 | DIP | — | TT | 50 | 65 | | 87.0% | 83.1% | 85.1% |
| Standard | 17467850 | SNP | A | T | 60 | 64 | | 93.8% | 91.0% | 92.4% |
| Standard | 17471411 | SNP | T | A | 41 | 46 | | 89.1% | 92.8% | 91.0% |
| Standard | 17472255 | SNP | A | G | 23 | 30 | | 76.7% | 88.7% | 82.7% |
| Standard | 17472390 | SNP | G | A | 28 | 33 | | 84.8% | 92.5% | 88.7% |
| Standard | 17473314 | SNP | A | C | 37 | 43 | | 86.0% | 90.5% | 88.3% |
| Standard | 17475319 | SNP | G | A | 48 | 55 | | 87.3% | 91.8% | 89.6% |
| Standard | 17478655 | SNP | G | A | 43 | 50 | | 86.0% | 90.5% | 88.3% |
| Standard | 17478717 | SNP | G | C | 50 | 59 | | 84.7% | 87.4% | 86.1% |
| Standard | 17478725 | SNP | C | G | 52 | 61 | | 85.2% | 87.4% | 86.3% |
| Standard* | 17478732 | Insertion | N/A | undefined element | 69 | 78 | | 88.5% | 88.8% | 88.7% |
| Standard | 17478744 | SNP | T | C | 53 | 58 | | 91.4% | 87.2% | 89.3% |
| Standard | 17478846 | SNP | T | C | 58 | 71 | | 81.7% | 86.2% | 84.0% |
| Standard | 17479513 | SNP | G | A | 44 | 49 | | 89.8% | 94.8% | 92.3% |
| Standard | 17479635 | SNP | C | A | 22 | 29 | | 75.9% | 92.6% | 84.3% |
| Standard | 17480177 | SNP | T | A | 50 | 59 | | 84.7% | 91.5% | 88.1% |
| Standard | 17480419 | SNP | A | G | 61 | 69 | | 88.4% | 93.5% | 91.0% |
| Standard | 17480510 | SNP | G | A | 73 | 89 | Ala68Val | 82.0% | 91.3% | 86.7% |
| Standard | 17480799 | SNP | G | A | 36 | 48 | | 75.0% | 93.6% | 84.3% |
| Standard | 17482187 | SNP | C | T | 63 | 72 | | 87.5% | 85.5% | 86.5% |
| Standard | 17482189 | SNP | C | A | 64 | 73 | | 87.7% | 85.5% | 86.6% |

TABLE 1-continued

| Pnome Source | Reference Position | Type | Reference allele (Lovell) | Pnome allele variant | Allele Counts | Read Coverage | Amino acid change | Pnome frequency | Opposing pnome frequency | Avg frequency |
|---|---|---|---|---|---|---|---|---|---|---|
| Standard | 17482202 | SNP | C | G | 72 | 83 | | 86.7% | 86.5% | 86.6% |
| Standard | 17483044 | SNP | G | A | 37 | 45 | | 82.2% | 90.5% | 86.4% |
| Standard | 17483142 | SNP | T | A | 31 | 32 | | 96.9% | 90.3% | 93.6% |
| Standard | 17483266 | SNP | G | T | 49 | 57 | | 86.0% | 95.0% | 90.5% |
| Pillar | 17629265 | SNP | C | A | 48 | 50 | | 96.0% | 88.4% | 92.2% |
| Standard | 18838626 | SNP | C | T | 37 | 45 | | 84.6% | 100.0% | 92.3% |
| Pillar | 19095800 | SNP | C | T | 25 | 29 | | 86.2% | 93.3% | 89.8% |
| Standard | 19183410 | SNP | C | T | 48 | 52 | Leu78Phe | 92.3% | 98.5% | 95.4% |
| Pillar | 19207473 | SNP | G | C | 104 | 106 | | 98.0% | 92.5% | 95.3% |
| Standard | 19277223 | SNP | A | C | 98 | 107 | Asn118His | 91.6% | 100.0% | 95.8% |
| Pillar | 19316667 | SNP | C | T | 66 | 67 | | 98.5% | 95.1% | 96.8% |
| Pillar | 19349347 | DIP | CACG | — | 45 | 48 | | 93.8% | 91.3% | 92.6% |
| Pillar | 19526986 | SNP | G | T | 26 | 26 | | 100.0% | 79.6% | 89.8% |
| Pillar | 19566458 | SNP | G | A | 30 | 32 | | 93.8% | 94.2% | 94.0% |
| Standard | 19652778 | SNP | C | A | 43 | 47 | | 91.5% | 100.0% | 95.8% |
| Pillar* | 19659067 | Insertion | N/A | undefined element | 55 | 55 | exon | 100.0% | 95.2% | 97.6% |
| Standard | 20128714 | SNP | G | A | 50 | 57 | | 87.7% | 95.2% | 91.5% |
| Pillar* | 20227738 | Insertion | — | AAAAT AAAAT | 26 | 27 | | 96.3% | 90.9% | 93.6% |
| Standard | 20565145 | DIP | A | — | 39 | 43 | | 95.9% | 91.5% | 93.7% |
| Pillar | 20800879 | SNP | C | T | 81 | 85 | | 95.3% | 95.4% | 95.4% |
| Pillar | 20846839 | SNP | C | T | 53 | 56 | 3'-utr | 94.6% | 95.7% | 95.2% |
| Standard | 21022090 | SNP | G | A | 44 | 47 | Ser177Leu | 93.6% | 96.7% | 95.2% |
| Pillar | 21505703 | DIP | T | — | 27 | 35 | | 96.9% | 86.4% | 91.7% |
| Pillar | 21840189 | SNP | T | A | 67 | 69 | | 97.1% | 86.0% | 91.6% |
| Pillar | 22046332 | SNP | T | A | 50 | 59 | | 84.7% | 91.5% | 88.1% |
| Standard | 22054901 | SNP | A | G | 51 | 66 | | 77.3% | 96.6% | 87.0% |
| Pillar | 22444084 | SNP | C | G | 48 | 52 | Leu54Val | 92.3% | 86.8% | 89.6% |
| Pillar | 22675832 | SNP | T | C | 70 | 80 | | 87.5% | 79.6% | 83.6% |
| Pillar | 22842934 | SNP | A | G | 45 | 48 | | 93.8% | 77.8% | 85.8% |
| Pillar | 23025274 | SNP | G | A | 35 | 38 | | 92.1% | 89.9% | 91.0% |
| Pillar | 23124200 | SNP | A | T | 34 | 37 | | 91.9% | 90.0% | 91.0% |
| Pillar | 24203115 | SNP | A | G | 83 | 90 | | 92.2% | 82.1% | 87.2% |
| Pillar | 24957082 | SNP | G | C | 62 | 71 | | 87.3% | 75.4% | 81.4% |
| Pillar | 25322275 | SNP | A | G | 46 | 58 | | 79.3% | 80.7% | 80.0% |
| Standard | 25732501 | SNP | G | A | 45 | 53 | | 84.9% | 85.7% | 85.3% |
| Standard | 26087634 | SNP | T | C | 52 | 66 | | 78.8% | 85.8% | 82.3% |
| Standard | 26378375 | SNP | T | C | 36 | 46 | | 78.3% | 83.3% | 80.8% |
| Pillar | 26402696 | SNP | C | A | 67 | 82 | His665Asn | 81.7% | 79.2% | 80.5% |

Structural variation analysis was performed using the CLC Genomics Workbench tool. A 5 Mb region (17 Mb-22 Mb) from both the vertical and standard pnome assemblies was extracted and used for the input. Default parameters were used and interchromosomal variation was excluded. The results were compared and filtered as described above.

Figure 3:
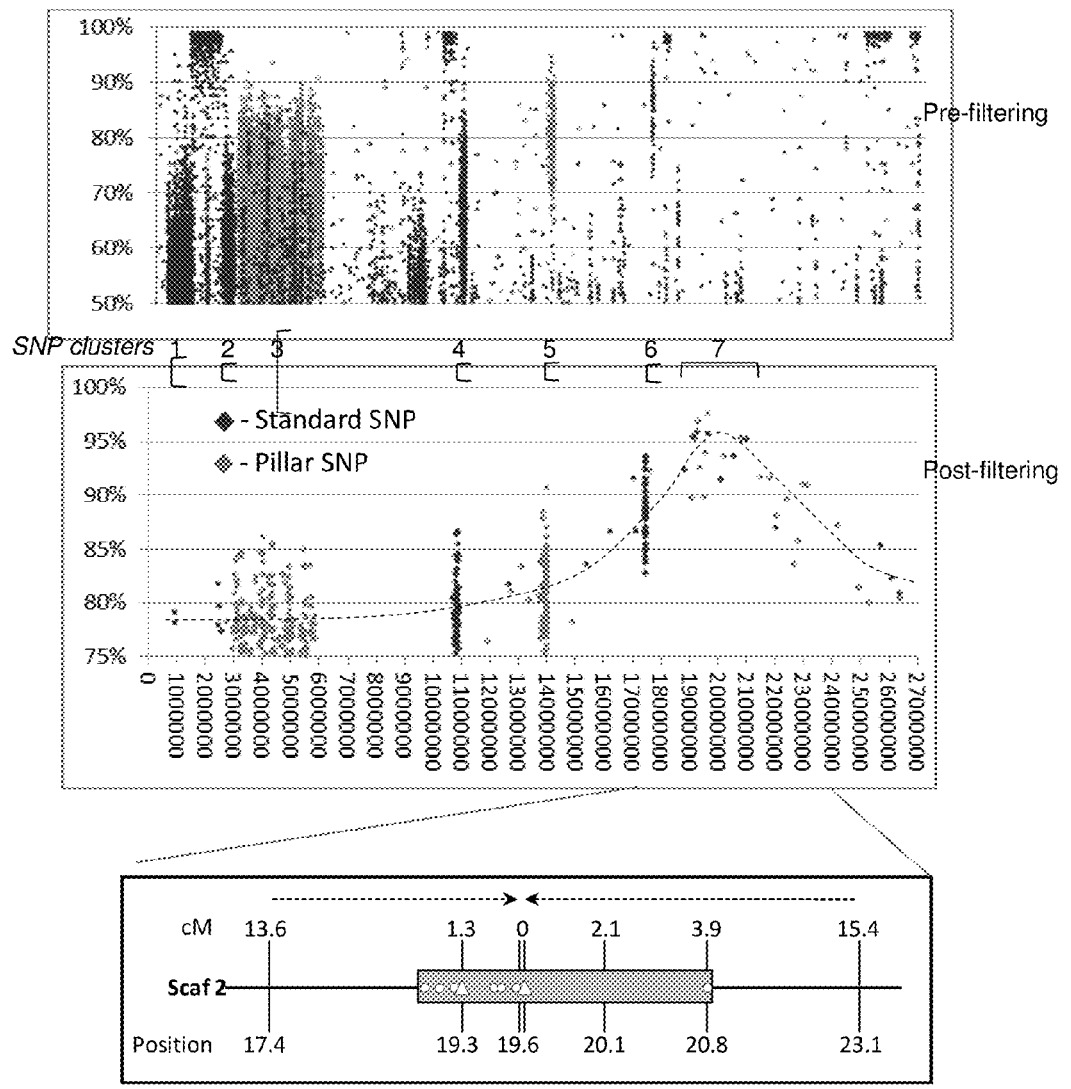
FIG. 3 depicts the SNP/DIP pnome frequency map for the peach vertical trait. SNPs/DIPs unique to pillar (ie. not present in the peach reference genome of the cultivar 'Lovell' or the standard pnome of 'True Gold') are shown in green while those unique to standard (ie. not found in peach reference genome 'Lovell' or the 'Italian pillar' pnome) are in red. Dashed line represents a trendline. A 2 Mb region (blue bar) was identified with the highest SNP frequencies. Genetic linkage map showing the HRM marker positions (blue) on scaffold 2 and the resulting calculated cM distances (red). Region delineated from the frequency map is indicated by shaded bar. SNPs within the mapped region are indicated by circles while DIPs are indicated with triangles.

Next, the pnomes were separately assembled against the peach genome (Verde et al., 2013, Nat Genet., doi: 10.1038/ng.2586) and subjected to pnome-wide Single Nucleotide Polymorphism (SNP) and Deletion Insertion Polymorphism (DIP) searches using CLC Genomics Workbench software (CLC Bio, Aarhus, Denmark). Approximately 300,000 SNPs and 36,000 DIPs were identified from both pnomes and filtered to identify linked polymorphisms. After filtering, a total of 487 SNPs and 23 DIPs remained and all were located on scaffold 2 (Table 1). The resulting average SNP/DIP frequencies were graphed by reference nucleotide position to reveal the physical location of the br gene responsible for the vertical trait (FIG. 3). The apparent unequal distribution of polymorphisms across scaffold 2 resulted in tight clusters of SNPs/DIPs unique to either the standard or the vertical pnomes. Still, the collective results showed a bell-shaped curve with a peak near the distal end of scaffold 2, position 20.0 Mb. A linkage cluster was also identified on the proximal end of scaffold 2, however, this region was excluded from further analysis as it showed a relatively lower level of linkage. Polymorphisms in the mapped region were rare with only 15 SNPs/DIPs identified within a 2 Mb interval. The defined position was consistent with previous vertical mapping studies which had positioned the trait on the distal half of scaffold 2 (Chaparro, J. X., et al., 1994, Theor. Appl. Genet. 87, 805-815; Sosinski B., et al., 2000, Theor. Appl. Genet. 101, 421-428; Sajer, O., et al., 2011, Plant Breeding, 131:186-192).

To confirm and further narrow the interval, seven HRM (High Resolution Melting) SNP markers spanning the region from 17.4 Mb to 23.1 Mb were designed from the pnome polymorphism data and tested on all 83 F2 individuals (56 pillar, 27 standard). Primers were designed from the pnome sequence to have an annealing temperature of 60° C. These are presented in Table 2. The HRM technique was performed in a single run on a LightCycler 480® (Roche Applied Science, Retrieved from the Internet: roche-applied-science-.com) in a reaction mix containing 2.5 ng of genomic DNA, 2 nM of each primer, and 1 mM $MgCl_2$ in the LightCycler 480 High Resolution Melting Master Mix with PCR-grade water adjusted to a total volume of 10 uL. The reaction conditions included an activation step at 95° C. for 10 min followed by 50 cycles of 95° C. for 15s, 60° C. for 15s, and 72° C. for 15 s. Before the HRM step, the products were heated to 95° C. for 1 min and cooled to 40° C. for 1 min. HRM was carried out over the range from 65° C. to 95° C., rising at 1° C. per second with 25 acquisitions per degree. All reactions were performed in 384-well microtiter plates. Individuals were scored based on their melting curve profiles relative to parental homozygous and heterozygous controls.

The results confirmed the accuracy of the allele frequency graph as the identification of recombinant individuals narrowed the causative polymorphism between positions 19.349 and 20.128 Mb (FIG. 3). Within the mapped interval, only two vertical SNPs remained, located at positions 19.526 Mb and 19.566 Mb, neither of which fell within or near annotated genes or predicted open reading frames. Based on the results, we hypothesized that the causative polymorphism could be a larger structural anomaly not revealed by the SNP or DIP searches. To assess this, we utilized the CLC Genomics Workbench—Structural Variation Detection tool to identify potential insertions, deletions, or rearrangements within a 5 Mb segment spanning the mapped interval (17.000 Mb and 22.000 Mb). A total of 95 putative structural polymorphisms were identified and filtered using the same method described for SNPs/DIPs. Ninety of the identified structural variations were found to be assembly artifacts arising from homopolymer or short repetitive regions. After filtering, 5 putative insertion events remained; 3 enriched in the standard pnome and 2 within the vertical pnome. Only one of the events specific to the vertical pnome fell within the mapped interval. It consisted of a putative insertion element that could be ascertained by the presence of unaligned flanking sequences on both ends of stacked reads. This insertion event had the highest vertical pnome frequency of all identified polymorphisms.

The putative insertion was located at position 19,659,067 by and fell within the 3rd exon of the predicted gene Ppa010082, annotated as encoding an unknown protein. The insertion site in Ppa010082 was marked by a short nucleotide repeat (GAT×7) within exon 3 that encodes a contiguous stretch of aspartic acid residues. Marker P19.659, that was designed to flank the insertion, confirmed that the element was present in all 56 vertical individuals and in none of the 27 standards. This marker along with HRM markers at positions P19.652 and P20.128 were tested on an additional 157 vertical individuals derived from several segregating populations with similar pedigrees to confirm the location. No recombinants were found for either the P19.652 or P19.659 markers. In contrast, 3 recombinants were identified for the P20.128 marker. Collectively, the pnome and marker mapping data excluded all but two SNP polymorphisms neither of which fell within or near gene sequences, indicating that the insertion event within Ppa010082 was highly likely to be the causative polymorphism for the vertical trait.

Ppa010082 was found to encode a predicted protein of 302 amino acids which was confirmed by the amplification of an approximately 900 bp band using RT-PCR and subsequent sequencing of the PCR product. Translation of the gene in pillar containing the insertion element in pillar results in a premature stop codon at amino acid position 102. Translation initiation from the 3' end of the insertion element leads to stop codons in all three reading frames prior to the resumption of the Ppa010082 coding sequence. BLAST® analysis of Ppa010082 indicated that it is present in diverse plant species and occurs most often as a single or low copy gene. Due to the similarities between TAC1 and Ppa010082 we named this peach orthologue PpTAC1 and identified as SEQ ID NO: 1.

Example 2

PpeTAC1 Gene Expression

Figure 4A:
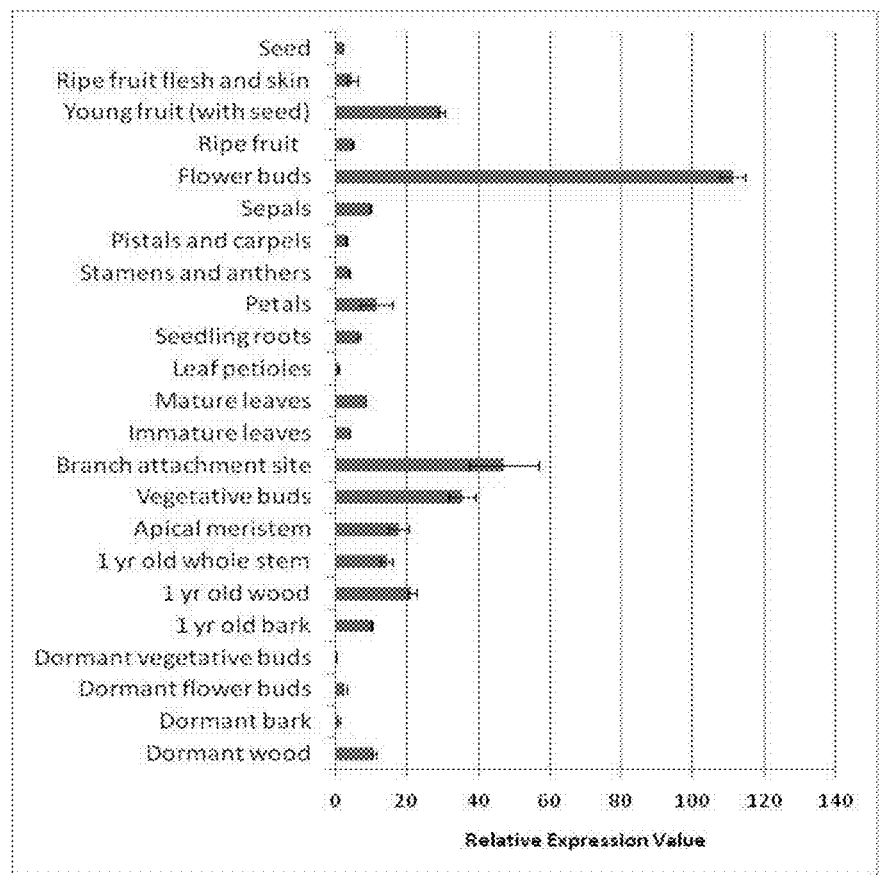
FIG. 4A depicts the expression of PpeTAC1 in anatomical tissues collected from the standard growth habit peach cultivar 'True Gold'. Tissues types are labeled. Y-axis represents relative expression values derived from qPCR results after normalization and standardization. Expression was highest in axillary flower and vegetative buds as well as axillary branch attachment sites.
Figure 4B:
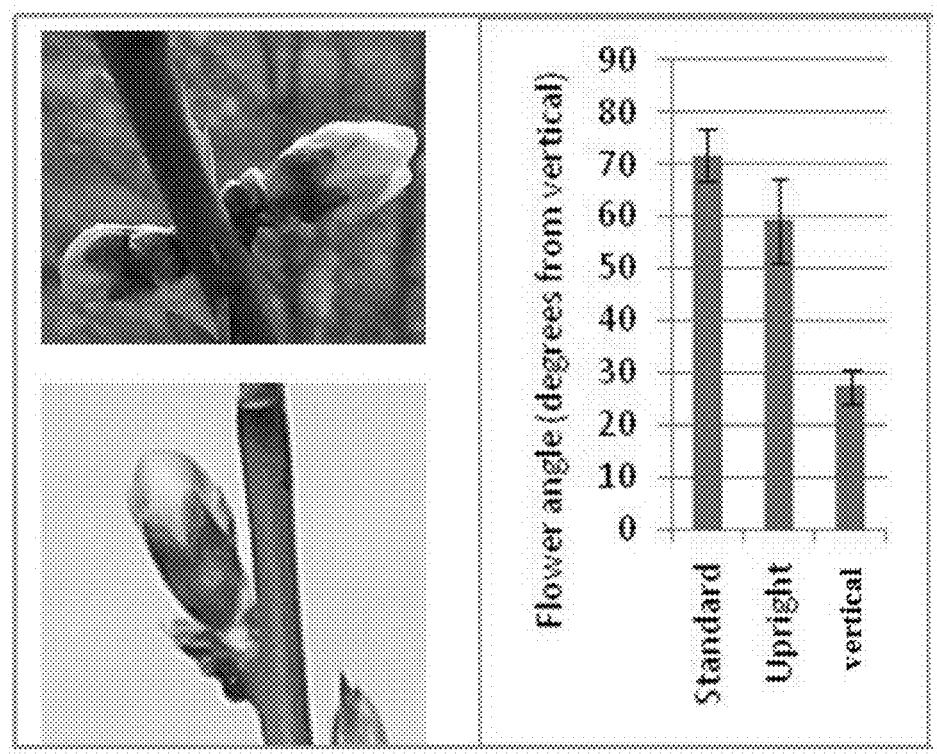
FIG. 4B depicts flower pedicel angles from standard (top left) and vertical (bottom left) trees. Quantitative differences in axillary floral bud emergence angles from vertical, upright, and standard trees are shown on right. Error bars represent standard deviation of three biological replicates derived from three independent trees.
Figure 4C:
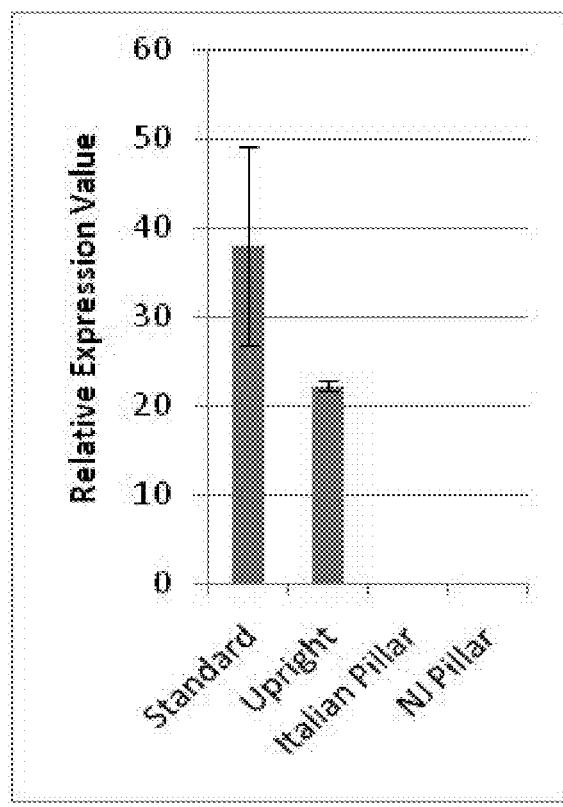
FIG. 4C is a graph depicting qPCR results for PpeTAC1 expression in branch attachment sites from verticle, upright, and standard trees. No transcript was detected in either 'Italian Pillar or "NJ Pillar" samples. Error bars represent standard deviation of three biological replicates.

To determine the expression pattern of PpeTAC1, qPCR studies were performed using a set of tissue samples collected from both vegetative and reproductive tissues of the standard growth habit doubled haploid cultivar 'True Gold' at various stages of growth and development (FIGS. 4A-C).

RNA extraction and qPCR was performed as previously described by Dardick et al., 2010. Briefly, each reaction was run in triplicate using 50 ng of RNA in a 15 pl reaction volume using the Superscript III Platinum SYBR Green qRT-PCR Kit (Applied Biosystems, Retrieved from the Internet: appliedbiosystems.com). The reactions were performed on a 7900DNA Sequence detector (Applied Biosystems, www.appliedbiosystems.com). Quantification was performed using a relative curve derived from a standard RNA run in parallel. A primer set designed to amplify 26S ribosomal RNA was run on all samples and used to normalize the data. A dissociation curve was run to verify that a single desired amplified product was obtained from each reaction. Primers used for ppTAC1 qPCR and for amplification of full length transcript are presented in Table 2.

Significant expression was observed in axillary tissues including vegetative buds, branch nodes, apical meristems, young fruit and flower buds. The high expression level of PpeTAC1 in flower buds is consistent with the nearly plagiotropic growth of the flower pedicels in standard trees compared to the narrow growth angles in the vertical mutants where the flower pedicels grew nearly parallel with stems (FIG. 4B). Interestingly, PpeTAC1 shows a relative high level of expression in attachment sites of actively growing branches where its role in the control of vertical branching orientation versus horizontal branching orientation may be required. In contrast, very low relative expression levels of PpeTAC1 were observed in mature or dormant tissues suggesting it is specific to actively growing tissues (FIG. 4A). Collectively, these data indicate that PpeTAC1 is specifically expressed within or near actively growing axillary vegetative and reproductive tissues.

Figure 6:
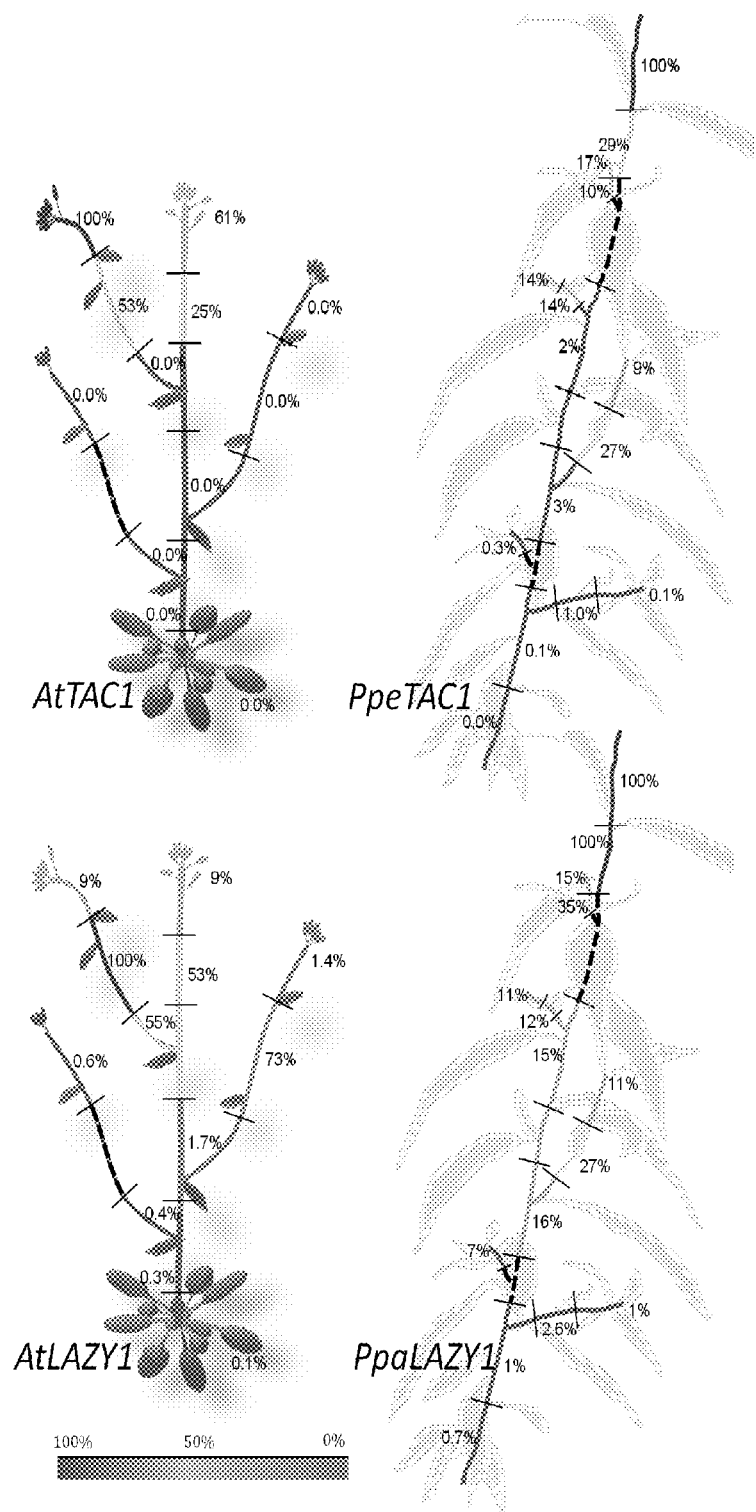
FIG. 6 is a depiction of the expression of TAC1 and LAZY1 in dissected 4 week old wild-type *Arabidopsis* (Col-0) plants and 4 month old peach saplings (cv. True Gold). Short black lines indicate cut points where sections of each individual plant were dissected and flash frozen. *Arabidopsis* image is a redrawn representation of an individual plant whereas the peach image is derived from an actual picture of the plant that was dissected. Expression values obtained for each segment via qPCR are color coded according to an expression scale (bottom). RNA could not be recovered from a small number of samples which are highlighted with dashed lines.

To assess the spatial expression patterns of TAC1, the primary shoot and all lateral shoots of five week old mature *Arabidopsis* plants and 12 week old peach seedlings were dissected into terminal, central, and basal sections and subject to qPCR analyses (FIG. 6). Results showed that TAC1 expression patterns are similar in both peach and *Arabidopsis* as expression was predominately in the apical shoots and the upper sections of the main stem and as well as in the upper laterals. In contrast, lower lateral shoots and the basal sections of the main trunk showed little or no expression. TAC1 expression was most prevalent in and near the apical meristems To test whether PpeTAC1 gene expression is altered in vertical cultivars, transcript levels were measured via qPCR. RNAs were extracted from branch attachment sites collected from one year old field grown shoots of vertical, upright, and standard stature trees. PpeTAC1 transcript could not be detected in either 'New Jersey Pillar' or 'Italian Pillar'. Similarly, transcript levels in the heterozygous upright trees were reduced relative to standard controls (FIG. 4C).

The lack of expression in 'NJ Pillar' prompted us to assess whether this cultivar possessed the same insertion element found in 'Italian Pillar'. Previous mapping studies had positioned the 'NJ Pillar' trait to the same region (Sosinski B., et al., 2000, *Theor. Appl. Genet.* 101, 421-428). The results of mapping studies were confirmed through hybridization tests for allelism which indicated that the same locus was responsible for the vertical trait in 'NJ Pillar' and 'Italian Pillar' (Sosinski B., et al., 2000, *Theor. Appl. Genet.* 101, 421-428).

Figure 4D:
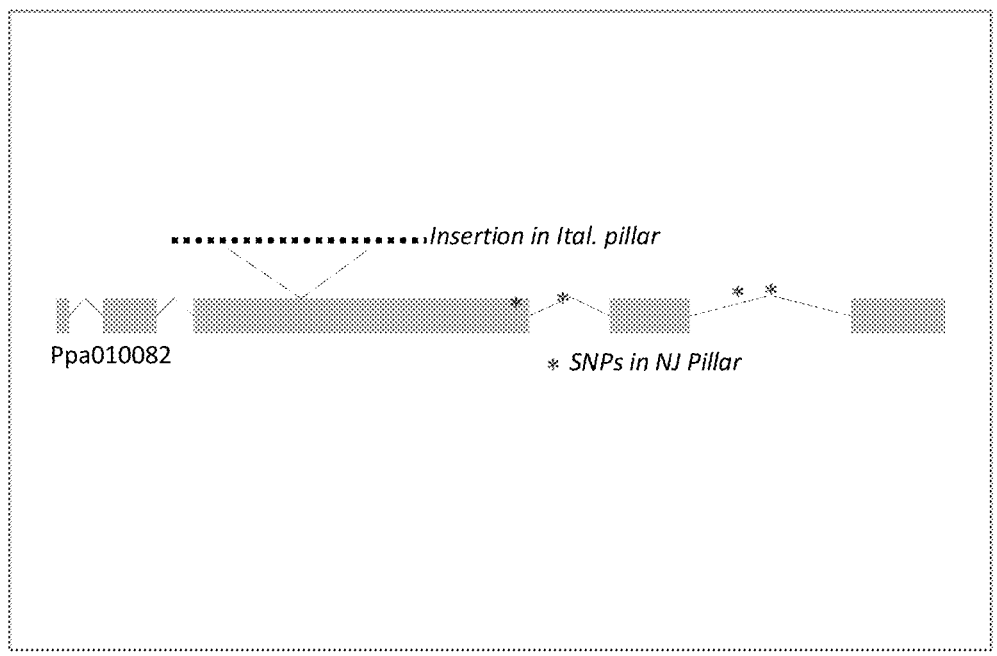
FIG. 4D is depiction of mutations in PpTAC1 are associated with the vertical phenotype.
Figure 5:
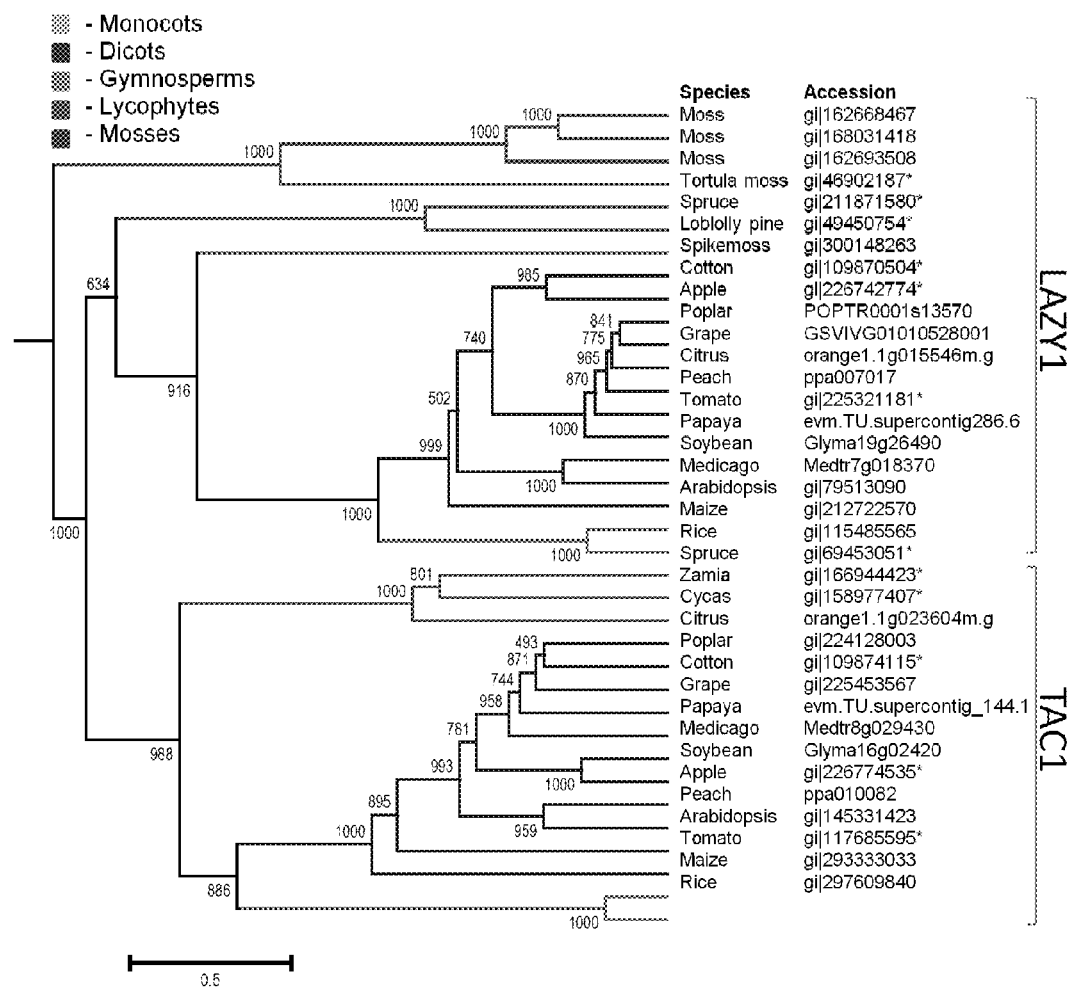
FIG. 5 is a phylogenetic tree of various IGT family members identified in diverse plant species. Tree was constructed using the UPGMA algorithm from an amino acid multiple alignment generated using CLC Genomics Workbench (CLC Bio, Netherlands). TAC1 and LAZY1 clades are indicated on right. Plant classifications are color coded according to the legend.

A 3 kb genomic fragment of PpeTAC1 was PCR amplified and sequenced from 'NJ Pillar'. Surprisingly, the insertion element present in 'Italian Pillar' was not found. Instead, PpeTAC1 in 'NJ Pillar' contained four novel SNPs within the 3rd and 4th introns (FIG. 4D). While none of the SNPs showed obvious deleterious impacts, one SNP was located at a position near the predicted intron 3 donor splice site and could potentially lead to transcript instability.

Example 3

Transformation of Plum Species

Silencing of PpeTAC1 in Plum.

PpeTAC1 specific primer sequences [5'-TGGGTTTGCTGGGAATGTGA-3' (SEQ. ID. NO. 22)] and [Rev 5'-CAGCTGGTTTCTGAACAATGGC-3' (SEQ. ID. NO. 23)] were used to PCR amplify a 300 base pair cDNA fragment from peach genomic DNA. The resulting fragment was cloned into the pENTR-D TOPO (Invitrogen) vector per manufacturer's specifications and sequenced for verification. An RNAi silencing vector was created using Gateway recombination technology (Invitrogen). PpeTAC1_300 pENTR-D TOPO was recombined with pHellsgate 8 (Commonwealth Scientific and Industrial Research Organisation (CSIRO), Australia) to create PpeTAC1-HG. This construct contains an inverted repeat of the 300 bp PpTAC1 fragment separated by an *Arabidopsis thaliana* pyruvate dehydrogenase kinase (PDK) intron. This arrangement is driven by a 35S promoter and is transcriptionally terminated by an octopine synthase (OCS) terminator. Expression of the resulting hairpin induces RNAi silencing and results in suppression of the native *Prunus* TAC1 gene.

Figure 7:
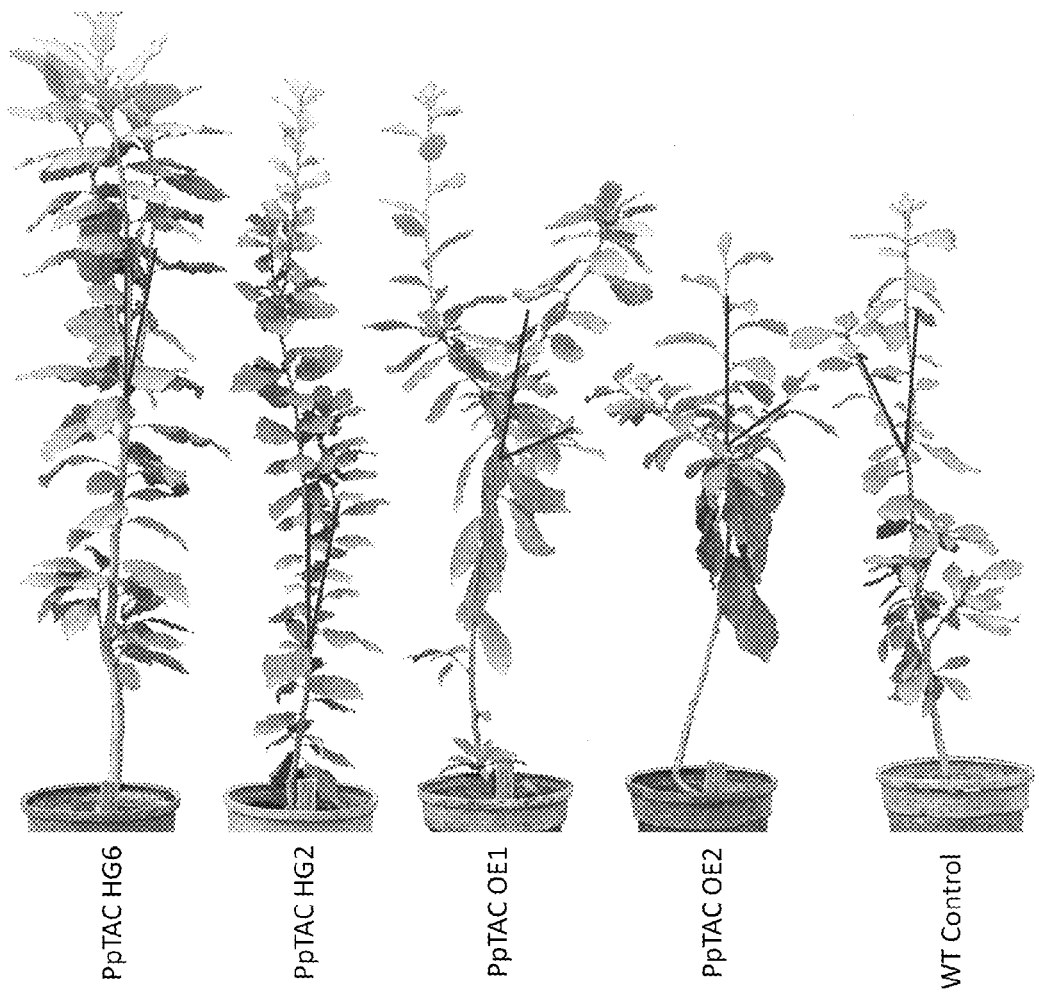
FIG. 7 is a depiction of four transgenic plum lines having PpeTAC1 silenced. The wild type depicted is a Bluebyrd plum line.

Plum transformation was performed as previously reported in Petri et al., 2008, Mol Breeding 22: 581-591 2008 and incorporated herein by reference. Using *Agrobacterium* mediated transformation of plum hypocotyl slices, four independent transgenic plum lines were obtained, two of which exhibited phenotypes identical to the peach pillar phenotype (FIG. 7). Such vertical growth habit is not known to occur in *Prunus domestica* germplasm.

Over-Expression of PpeTAC1 in Plum.

PpeTAC1 specific primer sequences [For 5'-GAATTCAATTCGCTCACAAAATATGAAG-3' (SEQ. ID. NO. 25)] and (Rev 5'-CCTTGTGTGCACTGAATTAAGGATCC-3' (SEQ. ID. NO. 26) were used to PCR amplify the full length PpeTAC1 coding sequence from peach RNA purified from apical shoots. The resulting fragment was cloned into a modified pBIN-ARS vector behind the Cauliflower Mosaic Virus 35S promoter. The resulting construct (called PpeTAC1-OE) was transformed into *Agrobacterium tumefaciens* for subsequent plum transformation.

Plum transformation was performed as previously reported (Petri et al., 2008) using *Agrobacterium* mediated transformation of plum hypocotyl slices. Two independent transgenic plum lines were obtained, both of which exhibited wide angle lateral shoot growth (FIG. 7).

Branch Angle Measurements.

Figure 8:
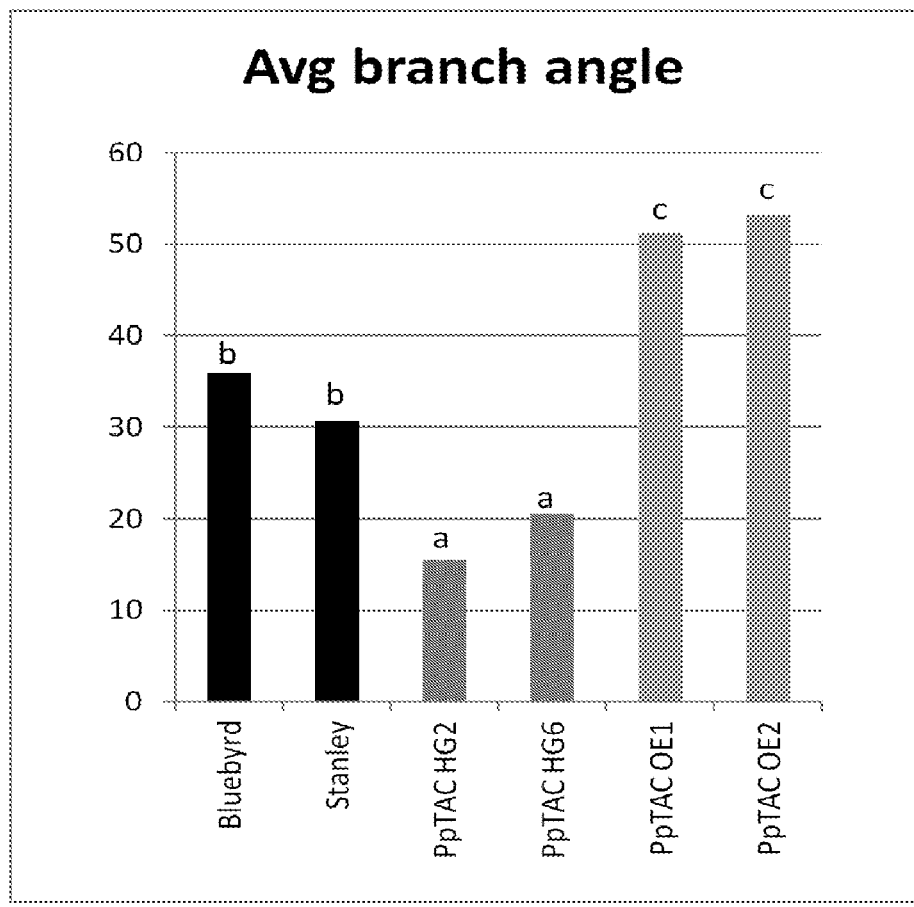
FIG. 8 is a measurement of the average branch angle for four transgenic plum lines. The wild type depicted is a Bluebyrd plum line.

To confirm that PpTAC1 silencing and over-expression alters lateral branch angles in plum, measurements of vegetatively propagated transgenic lines were taken on 1 year old greenhouse grown trees. Branch angles were quantified using a compass with 90° representing branches growing at right angles and 0° representing absolute vertical growth. Mean branch growth angles in 2 PpeTAC-HG lines, 2 PpeTAC-OX lines, and 2 control lines are shown in FIG. 8. Lower case letters designate statistically significant groups ($P$-value<0.05) derived from pairwise T-tests and ANOVA. Collectively the results confirm that silencing of PpeTAC1 produces a more upright tree form (branch angle<22°) while over-expression of PpeTAC1 leads to wider branch angles (branch angle>50°).

Gene Expression

Figure 9:
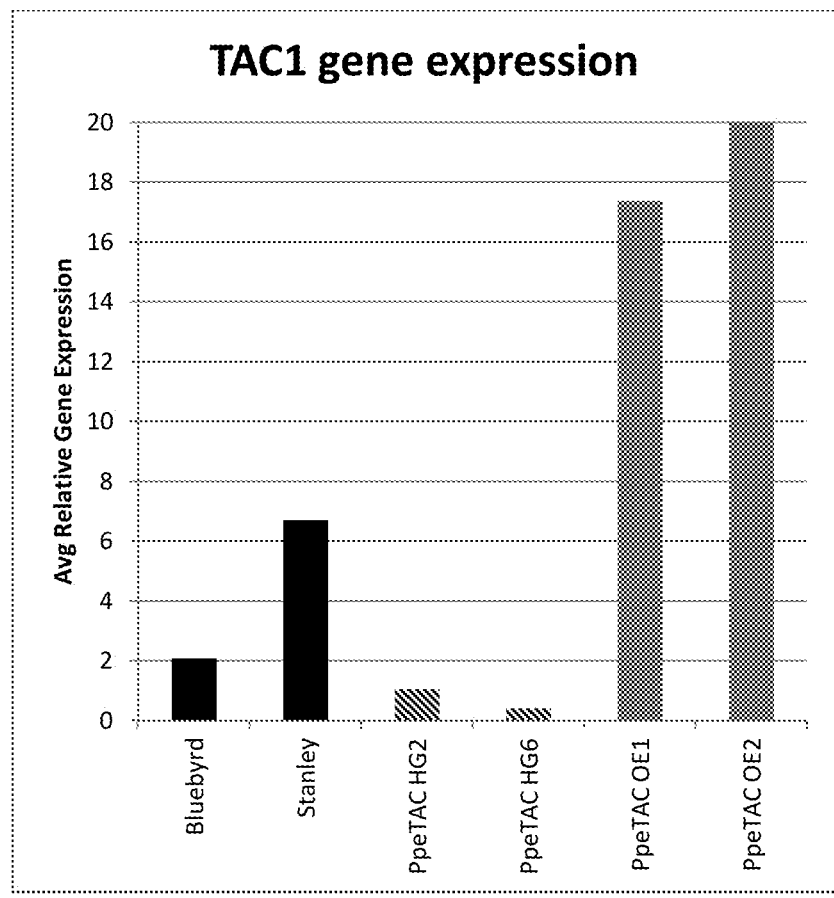
FIG. 9 is graph depicting RT-quantitative PCR on four transgenic plum line.

To confirm silencing or overexpression of PpeTAC1 in transgenic plums, real-time quantitative polymerase chain reaction (qPCR) was performed on plum transgenic and control lines (FIG. 9). Total RNA was extracted from apical shoots of 1 year old, greenhouse grown plants using the SQ Total RNA Extraction Kit (Omega Biotech, Norcross Ga.) per manufacturer's instructions. qPCR from total RNA was performed using the CYBR Green One—Step qPCR Kit (Invitrogen, Carlsbad Calif.) and run in an ABI 7900HT Sequence Detection System. Each reaction was run in triplicate using 50 ng of RNA. Three independent vegetatively propagated plants from each line (PpeTAC1 HG2, PpeTAC1 HG6, PpeTAC1 OE1, and PpeTAC1 OE2) were tested. Quantification was performed using a relative curve derived from a serially diluted standard RNA run in parallel. A dissociation curve was run to verify that a single desired amplified product was obtained from each reaction. The PpeTAC1 primers used (For 5'-TTTGCCAAGAAACTCATCCCTCGC (SEQ. ID. NO. 18) and Rev 5'-GCTGCTTCTGGCCATCTGATTTGT (SEQ. ID. NO. 19)) were designed to amplify both the PpeTAC1 transgene and the native plum TAC1 gene. FIG. 9 shows the normalized relative gene expression value for each transgenic line. The results confirm that TAC1 gene expression is repressed in the transgenic lines containing the RNAi hairpin (PpeTAC1 HG2 and PpeTAC1 HG6) and that PpeTAC1 is over expressed in transgenic plum lines containing PpeTAC1 under the control of a 35S promoter (PpeTAC1 OE1 and PpeTAC1 OE2).

While the invention has been described with reference to details of the illustrated embodiment, these details are not intended to limit the scope of the invention as defined in the appended claims.

The embodiment of the invention in which exclusive property or privilege is claimed is defined as follows:

1. An isolated or recombinant cDNA molecule, wherein said cDNA molecule encodes a polypeptide of SEQ ID NO:27.

2. The isolated or recombinant cDNA molecule of claim 1, wherein said cDNA molecule is by SEQ ID NO:1.

3. An expression construct comprising the isolated or recombinant cDNA molecule of claim 1 or 2 operably linked to a promoter sequence.

4. A host cell comprising the expression construct of claim 3.

5. The host cell of claim 4, wherein said host cell is a *Prunus* cell.

6. The host cell of claim 5, wherein said host cell is a cell from *Prunus persica, Prunus domestica, Prunus avium, Prunus salicina* and *Prunus armeniaca*.

7. A method of producing a *Prunus* plant having horizontally oriented branches, said method comprising:
constructing a recombinant vector comprising a construct comprising the isolated or recombinant cDNA molecule of claim 1 or 2 operably linked to a Cauliflower Mosaic Virus 35S promoter;
transforming *Prunus* plant cells with the recombinant vector;
regenerating the plant cells into a plant; and
growing the transgenic *Prunus* plant wherein overexpression of the cDNA molecule results in said transgenic plant having a horizontal phenotype characterized by axillary shoots having an increased horizontal orientation relative to a non-transformed control plant.

8. An RNAi construct comprising an isolated or recombinant cDNA molecule, wherein said molecule has the nucleotide sequence of SEQ ID NO:24.

9. A vector comprising the RNAi construct of claim 8.

10. A host cell comprising the vector of claim 9.

11. The host cell of claim 10, wherein said host cell is a *Prunus* cell.

12. The host cell of claim 11, wherein said host cell is a cell from *Prunus persica, Prunus domestica, Prunus avium, Prunus salicina* or *Prunus armeniaca*.

13. A method of producing a *Prunus* plant having horizontally oriented branches, said method comprising:
transforming *Prunus* plant cells with the vector of claim 9;
regenerating the plant cells into a plant; and
growing the plant, wherein expression of the construct induces RNA interference (RNAi) in the plant, resulting in plants having a horizontal phenotype characterized by axillary shoots having an increased horizontal orientation relative to a non-transformed control plant.

14. A transgenic plant produced by the method of claim 13 or the progeny thereof, wherein said plant or progeny contain the construct and exhibit changed plant architecture with horizontally oriented branches compared to a wild-type non transformed *Prunus* plant.

15. A transgenic seed comprising the RNAi construct of claim 8.

16. A Plant[s], plant cell[s], plant part[s], or plant seed[s] produced by *Prunus persica, P. domestica, P. avium, P. salicina* and *P. armeniaca* plants which have been transformed by the RNAi construct of claim 8, wherein said plant, plant cell, plant part or plant seed contain the construct.

* * * * *